US008187279B2

(12) United States Patent
Livorsi et al.

(10) Patent No.: US 8,187,279 B2
(45) Date of Patent: May 29, 2012

(54) SURGICAL INSTRUMENT SYSTEM WITH BALL AND SOCKET SUPPORT

(75) Inventors: Carl F. Livorsi, Lakeville, MA (US); Joseph G. Wyss, Fort Wayne, IN (US); Normand T. Brisebois, Westport, MA (US); Mark A. Capobianco, Westport, MA (US); Michael J. Fortin, Acushnet, MA (US); Kenneth R. Hayes, Fall River, MA (US); James M. Kennedy, Berkley, MA (US); John J. McMorrow, Franklin, MA (US); Paul J. Monteiro, Somerset, MA (US); Jean-Pierce Nuss, North Dartmouth, MA (US); Phillip G. Withee, Fall River, MA (US)

(73) Assignee: Depuy Products, Inc., Warsaw, IN (US)

( * ) Notice: Subject to any disclaimer, the term of this patent is extended or adjusted under 35 U.S.C. 154(b) by 702 days.

(21) Appl. No.: 11/926,892

(22) Filed: Oct. 29, 2007

(65) Prior Publication Data
US 2008/0132897 A1 Jun. 5, 2008

Related U.S. Application Data

(60) Provisional application No. 60/863,694, filed on Oct. 31, 2006, provisional application No. 60/863,711, filed on Oct. 31, 2006.

(51) Int. Cl.
*A61B 17/58* (2006.01)
*A61B 17/60* (2006.01)
*A61B 1/32* (2006.01)
*A61F 2/00* (2006.01)

(52) U.S. Cl. .......................................... 606/88; 600/233

(58) Field of Classification Search .................... 606/88, 606/82, 87; 600/207, 221, 233
See application file for complete search history.

(56) References Cited

U.S. PATENT DOCUMENTS

| 1,279,803 | A | * | 9/1918 | Watson | 248/160 |
| 3,762,404 | A | | 10/1973 | Sakita | |
| 3,858,578 | A | * | 1/1975 | Milo | 600/229 |
| 4,106,499 | A | * | 8/1978 | Ueda | 600/499 |
| 4,373,709 | A | | 2/1983 | Whitt | |
| 4,407,277 | A | | 10/1983 | Ellison | |
| 4,457,300 | A | * | 7/1984 | Budde | 600/228 |

(Continued)

FOREIGN PATENT DOCUMENTS

EP 0677274 A2 2/1995

(Continued)

OTHER PUBLICATIONS

European Search Report From Corresponding EPO Patent Application No. 07254308.5-2310/1917920, Dated Oct. 8, 2010, 8 Pages.

(Continued)

*Primary Examiner* — Thomas C. Barrett
*Assistant Examiner* — David Bates

(57) ABSTRACT

A surgical instrument support system has a support frame supported by three arms. Each arm has a plurality of ball and socket members strung in series along a cable. The arms are also connected to bases mountable to the patient's limb on the proximal and distal sides of the joint. Actuators are provided for each arm to change the tension in the cables to change the stiffness of each arm. The support system can be part of a surgical instrument system that includes a plurality of resection guides mountable to the support frame.

22 Claims, 14 Drawing Sheets

U.S. PATENT DOCUMENTS

| | | | |
|---|---|---|---|
| 4,545,573 A | 10/1985 | Murphy | |
| 4,615,516 A | 10/1986 | Stulberg et al. | |
| 4,949,927 A | 8/1990 | Madocks et al. | |
| 5,007,912 A | 4/1991 | Albrektsson et al. | |
| 5,010,900 A | 4/1991 | Auchinleck et al. | |
| 5,063,918 A | 11/1991 | Guhl | |
| 5,085,214 A * | 2/1992 | Barrett | 5/648 |
| 5,154,717 A | 10/1992 | Matsen et al. | |
| 5,290,220 A * | 3/1994 | Guhl | 602/33 |
| 5,514,143 A | 5/1996 | Bonutti et al. | |
| 5,569,176 A * | 10/1996 | Graham | 602/32 |
| 5,616,146 A * | 4/1997 | Murray | 606/80 |
| 5,876,333 A * | 3/1999 | Bigliani et al. | 600/231 |
| 5,906,586 A * | 5/1999 | Graham | 602/32 |
| 5,950,628 A * | 9/1999 | Dunfee | 128/874 |
| 5,954,638 A * | 9/1999 | Spranza, III | 600/201 |
| 6,066,107 A | 5/2000 | Habermeyer | |
| 6,071,295 A * | 6/2000 | Takahashi | 606/191 |
| 6,210,325 B1 * | 4/2001 | Bartie et al. | 600/229 |
| 6,308,353 B1 | 10/2001 | Van Steenburg | |
| 6,478,799 B1 | 11/2002 | Williamson | |
| 6,551,325 B2 | 4/2003 | Neubauer et al. | |
| 6,626,830 B1 * | 9/2003 | Califiore et al. | 600/229 |
| 6,882,878 B2 * | 4/2005 | Schmit et al. | 600/415 |
| 6,964,073 B1 * | 11/2005 | Curry | 5/626 |
| 7,294,104 B2 * | 11/2007 | Person | 600/227 |
| 7,458,977 B2 * | 12/2008 | McGinley et al. | 606/130 |
| 7,476,199 B2 * | 1/2009 | Spence et al. | 600/210 |
| 2002/0068942 A1 | 6/2002 | Neubauer et al. | |
| 2002/0077539 A1 | 6/2002 | Schmit et al. | |
| 2002/0133162 A1 | 9/2002 | Axelson et al. | |
| 2002/0133163 A1 | 9/2002 | Axelson et al. | |
| 2005/0216032 A1 | 9/2005 | Hayden | |
| 2006/0100562 A1 | 5/2006 | Pamplin | |
| 2007/0100346 A1 | 5/2007 | Wyss et al. | |
| 2007/0123896 A1 | 5/2007 | Wyss et al. | |

FOREIGN PATENT DOCUMENTS

| | | |
|---|---|---|
| EP | 0677274 A3 | 2/1995 |
| EP | 1444962 A2 | 8/2004 |
| EP | 1444962 A3 | 8/2004 |
| EP | 1444962 B1 | 1/2009 |
| WO | WO 02/07612 A1 | 1/2002 |
| WO | WO 2005/087116 A2 | 9/2005 |

OTHER PUBLICATIONS

Surgical Technique for Use With P.F.C. Sigma Knee Systems, Primary Cruciate-Retaining & Cruciate-Substituting Procedure, Specialist 2 Instrument, 1998 Depuy Orthopaedics, 4M0904, SP2-007 (Rev. 5), 102 Pages.

Codman Greenberg Retractor and Handrest, A Universal System, 1999 Codman & Shurtleff, Inc., N-408 3/04 DS/CSM, 6 Pages.

\* cited by examiner

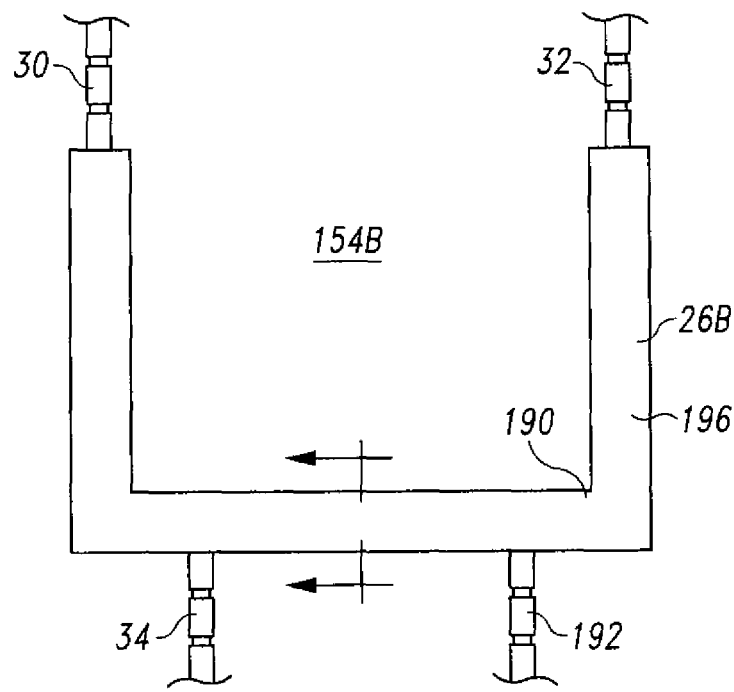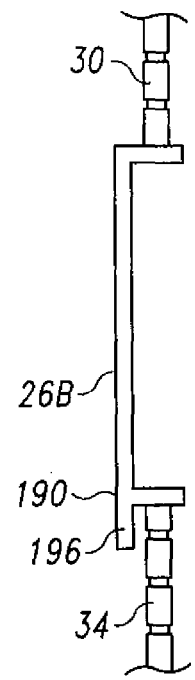
Fig. 28    Fig. 29
Fig. 30
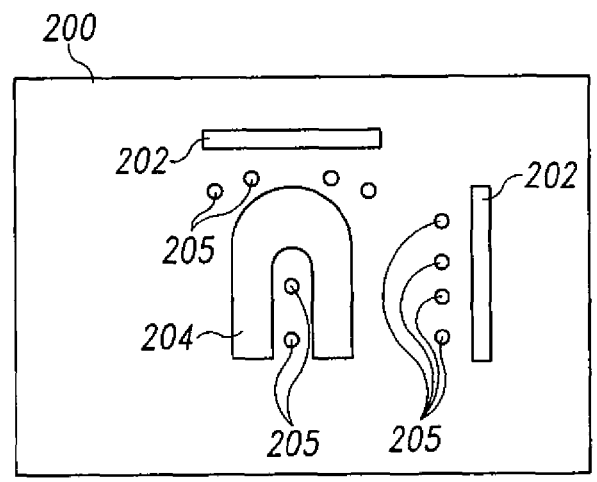
Fig. 31

SURGICAL INSTRUMENT SYSTEM WITH BALL AND SOCKET SUPPORT

CROSS-REFERENCE TO RELATED APPLICATIONS

This application claims priority to U.S. Prov. App. No. 60/863,694 filed Oct. 31, 2006, entitled "LIMB STABILIZING SYSTEM FOR ARTHROPLASTY," which is incorporated by reference herein in its entirety and to U.S. Prov. App. No. 60/863,711 filed Oct. 31, 2006, entitled "SURGICAL INSTRUMENT SYSTEM WITH BALL AND SOCKET SUPPORT," which is incorporated by reference herein in its entirety.

BACKGROUND OF THE INVENTION

The present invention relates to surgical instruments used to prepare a bone to receive a prosthetic implant, and more particularly, to such an instrument system.

When a skeletal joint is damaged, whether as a result of an accident or illness, a prosthetic replacement of the damaged joint may be necessary to relieve pain and to restore normal use to the joint. Typically the entire joint is replaced by means of a surgical procedure that involves removal of the ends of the corresponding damaged bones and replacement of these ends with prosthetic implants. This replacement of a native joint with a prosthetic joint is referred to as a primary total-joint arthroplasty.

The surgical preparation of the bones during primary total-joint arthroplasty is a complex procedure. A number of bone cuts are made to effect the appropriate placement and orientation of the prosthetic components on the bones. In total knee arthroplasty, the joint gaps in extension and flexion must also be appropriate.

In the case of total knee arthroplasty, cutting guide blocks are used in creating the bone cuts on the proximal tibia and distal femur. The position, alignment and orientation of the cutting blocks are important in ensuring that the bone cuts will result in optimal performance of the prosthetic implant components. Generally, a tibial cutting block is positioned, aligned and oriented so that the cutting guide surface is in the optimal proximal-distal position, posterior slope, and varus-valgus orientation. Depending on the type of prosthetic implant system to be used, one or more cutting blocks are also positioned, aligned and oriented on the distal femur to ensure appropriate positioning of the distal femoral implant component and appropriate joint gaps.

A variety of alignment guides and cutting blocks have been provided in the prior art for use in preparing bone surfaces in primary total-knee arthroplasty, including alignment guides and cutting blocks used in preparing the proximal tibia and distal femur.

Prior art instrument sets with alignment guides include the Specialist® 2 instruments (DePuy Orthopaedics, Inc., Warsaw, Ind.) for use with DePuy Orthopaedics' P.F.C.® Sigma Knee System. The extramedullary tibial alignment guide for this instrument system includes an ankle clamp, a pair of telescoping alignment rods and a cutting block. The ankle clamp is affixed about the patient's ankle, without extending through the patient's soft tissue. Parts of this system are manually adjustable: the proximal-distal position of the cutting block is adjusted by sliding the telescoping rods and then locking the rods in the desired position; posterior slope is set at the ankle by sliding the distal end of the alignment rod in an anterior-posterior direction to thereby pivot the cutting block into the desired orientation; varus-valgus slope is set by pivoting the cutting block so that the alignment guide pivots about a rod at the ankle clamp.

SUMMARY OF THE INVENTION

The present invention provides a surgical instrument system that can be used to efficiently and accurately set the position, alignment and orientation of resection guides and can that can be used to support other surgical instruments.

In one aspect, the present invention meets these objectives by providing a surgical instrument system comprising a support frame, a first arm, a first actuator, a second arm, a second actuator, a third arm and a third actuator. The first arm has first and second ends. The first end of the first arm is connected to the support frame and the second end of the first arm is connected to the first actuator. The first arm includes a tension member and a plurality of ball and socket members slidably strung along the tension member in series to form a plurality of articulatable linkages having a stiffness. The second arm also has first and second ends. The first end of the second arm is connected to the support frame and the second end of the first arm is connected to the second actuator. The second arm includes a tension member and a plurality of ball and socket members slidably strung along the tension member in series to form a plurality of articulatable linkages having a stiffness. The third arm has first and second ends. The first end of the third arm is connected to the support frame and the second end of the third arm is connected to the third actuator. The third arm includes a tension member having a plurality of ball and socket members slidably strung along the tension member in series to form a plurality of articulatable linkages having a stiffness. Activation of the first actuator changes the stiffness of the first arm, activation of the second actuator changes the stiffness of the second arm, and activation of the third actuator changes the stiffness of the third arm.

In another aspect, the present invention provides a surgical instrument system for resecting a portion of a bone at a joint of a patient's limb. The system comprises a proximal base, a distal base, a support frame, a resection guide, three arms and a tensioning mechanism. The proximal base is sized and shaped to be mountable on the exterior of the patient's limb on the proximal side of the joint. The distal base is sized and shaped to be mountable on the exterior of the patient's limb on the distal side of the joint. The resection guide is selectively mountable to the support frame. The first arm has first and second ends; the first end of the first arm is connected to the support frame and the second end of the first arm is connected to the proximal base. The first arm includes a tension member having first and second ends and a plurality of ball and socket members slidably strung along the tension member to form a plurality of articulatable linkages. The second arm has first and second ends; the first end of the second arm is connected to the support frame and the second end of the first arm is connected to one of the bases. The second arm includes a tension member having first and second ends and a plurality of ball and socket members slidably strung along the tension member to form a plurality of articulatable linkages. The third arm has first and second ends; the first end of the third arm is connected to the support frame and the second end of the third arm is connected to the distal base. The third arm includes a tension member having first and second ends and a plurality of ball and socket members slidably strung along the tension member to form a plurality of articulatable linkages. The tensioning mechanism is provided for increasing the tension in each tension member.

BRIEF DESCRIPTION OF THE DRAWINGS

The invention will be better understood by reference to the figures of the drawings wherein like numbers denote like parts throughout and wherein:

FIG. 28 is a top plan view of another alternative support frame that may be used in the systems of FIGS. 1 and 2;

FIG. 29 is a side elevation of the support frame of FIG. 28;

FIG. 30 is a side elevation of a mounting clamp of that may be used to mount a surgical implement such as the resection guide of FIG. 26 to the support frame of FIGS. 28-29;

FIG. 31 is a top plan view of an alternative resection guide that may be used with the support frame of FIGS. 28-29;

DETAILED DESCRIPTION OF THE ILLUSTRATED EMBODIMENTS

Figure 1:
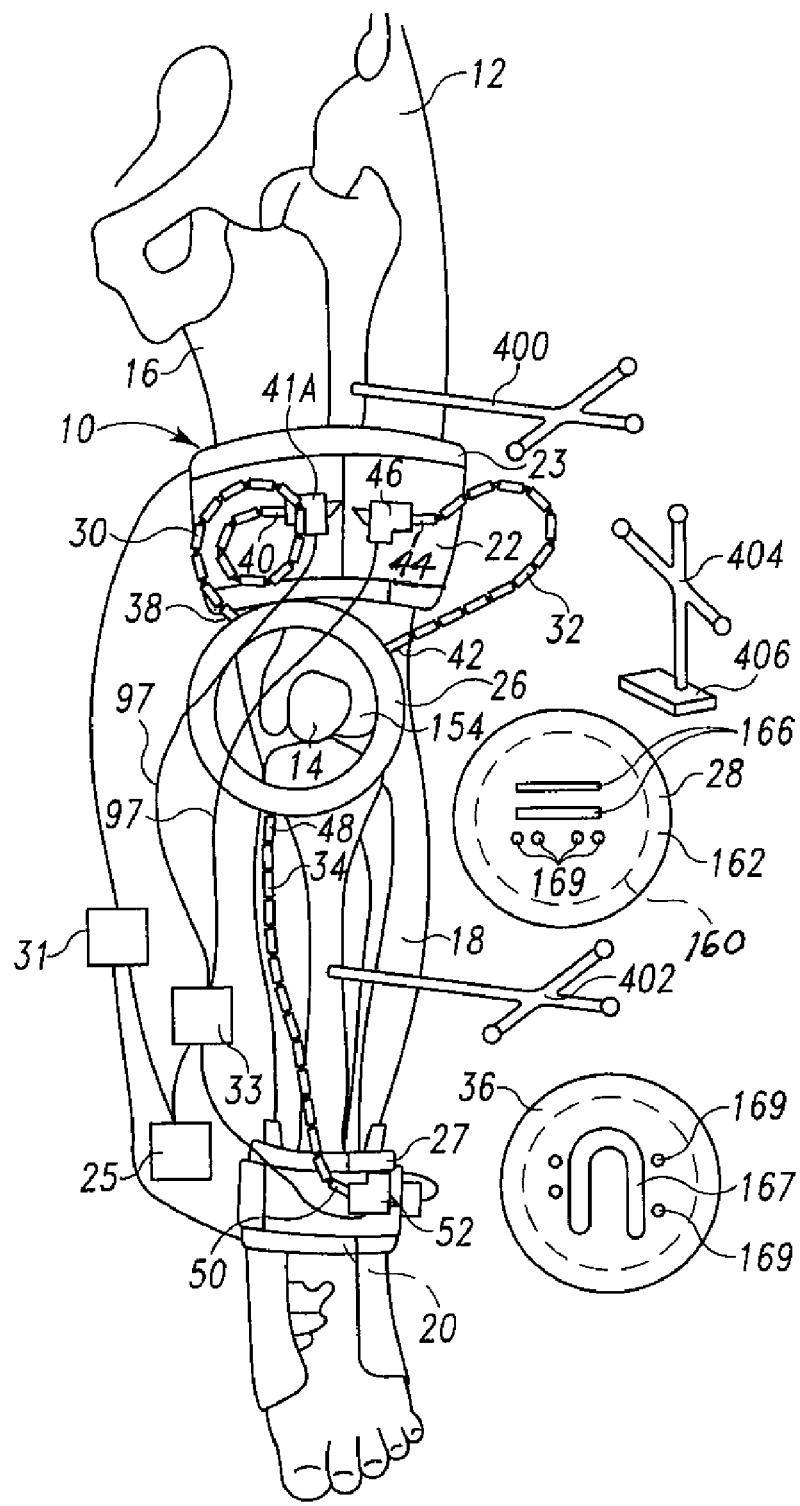
FIG. 1 is an anterior view of a patient's leg, showing a part of a first embodiment of the surgical instrument support system of the present invention mounted on the patient's leg with the leg in extension, with other parts of the surgical instrument system shown adjacent to the patient's leg and with optional accessories for computer assisted surgery shown mounted to the patient's leg and adjacent to the patient's leg.
Figure 2:
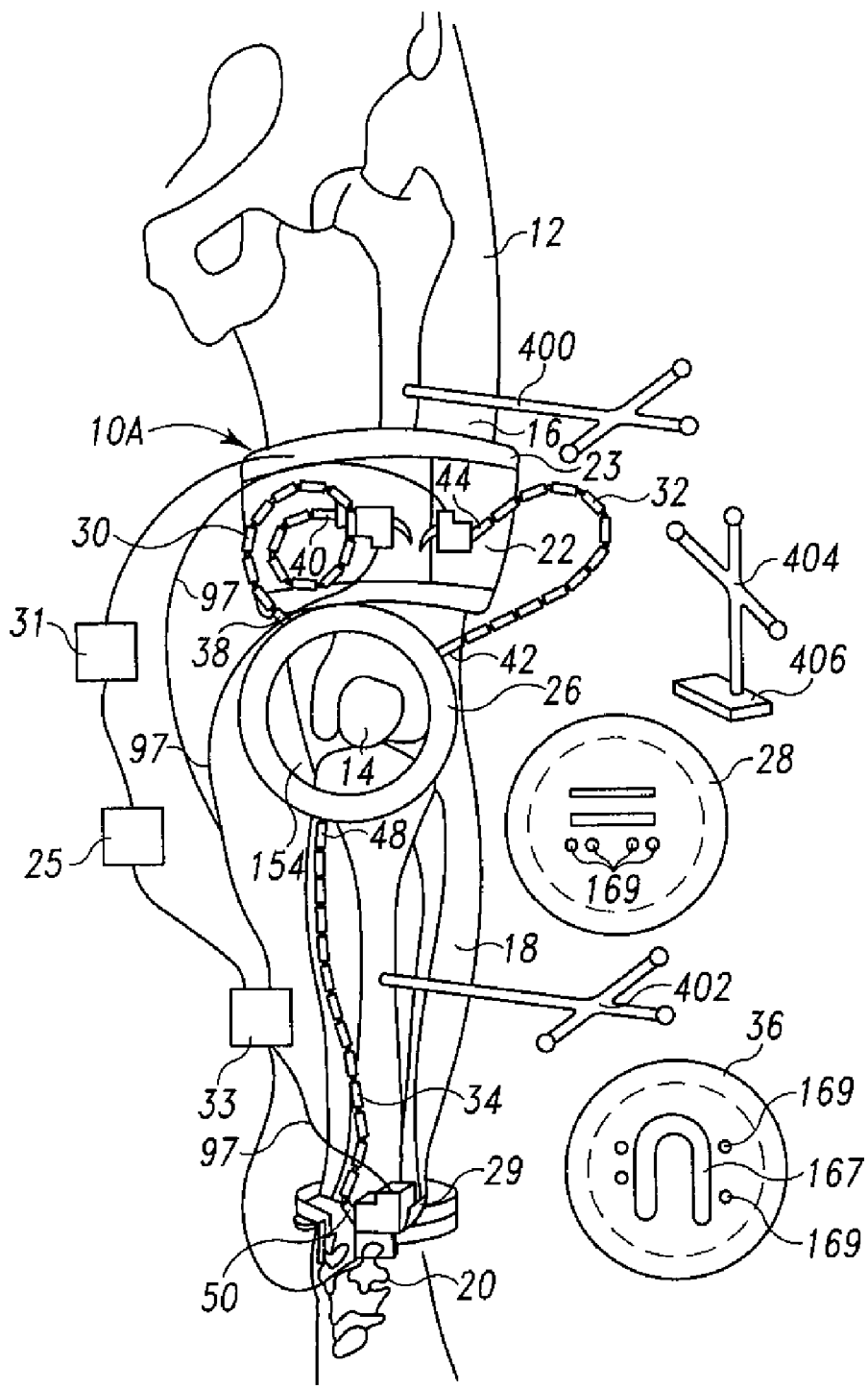
FIG. 2 is a view similar to FIG. 1, showing a second embodiment of a surgical instrument system according to the present invention, with other parts of the surgical instrument system shown adjacent to the patient's leg and with optional accessories for computer assisted surgery shown mounted to the patient's leg and adjacent to the patient's leg.
Figure 3:
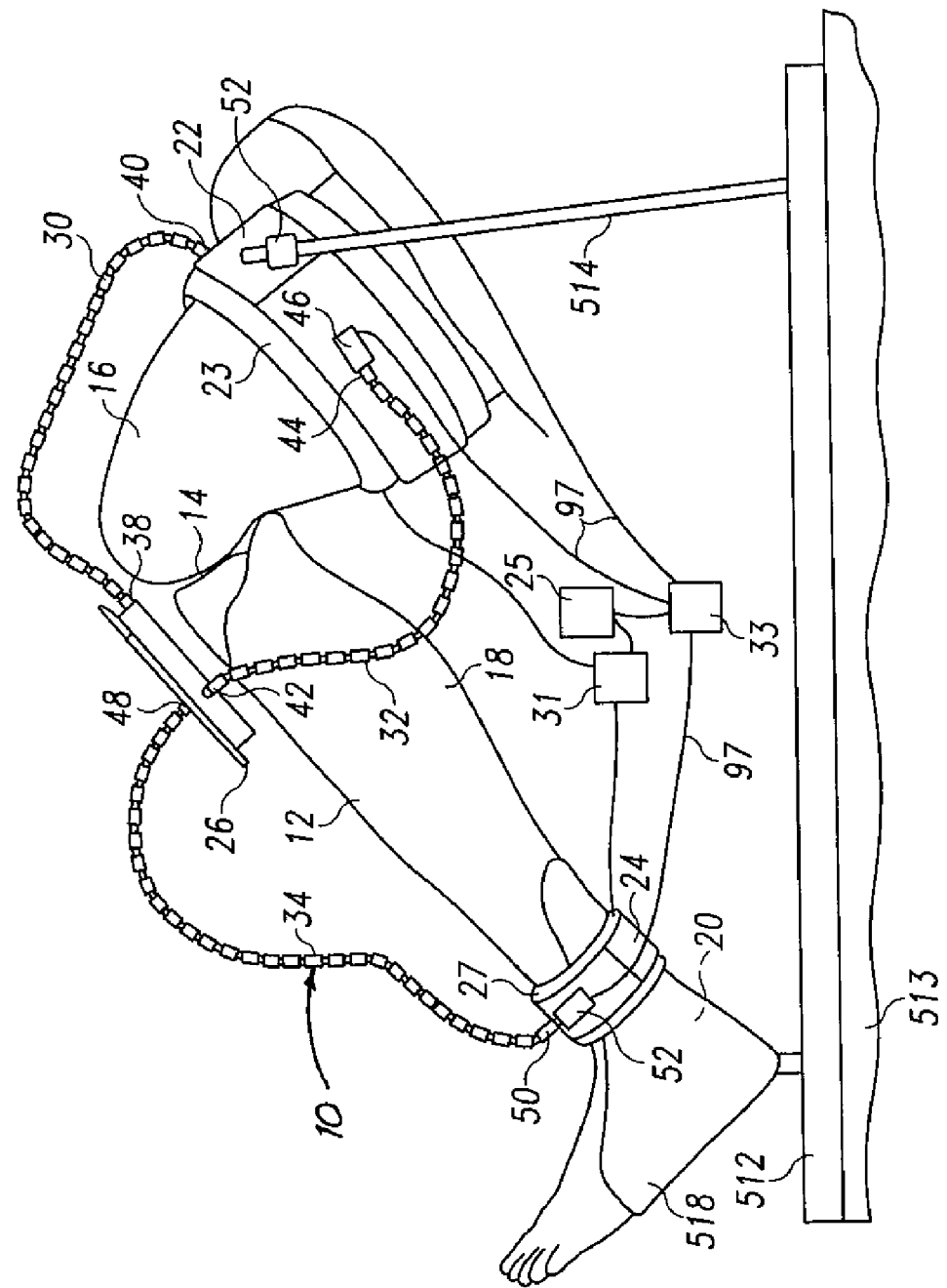
FIG. 3 is an elevation, from the lateral side of the patient's leg showing the patient's leg in flexion with the surgical instrument support system of FIG. 1 mounted on the patient's leg, the surgical instrument support system being shown with an alternative set of actuators and with a system for fixing and stabilizing the position of the patient's leg.

A first embodiment of a system illustrating the principles of the present invention is illustrated at 10 in FIGS. 1 and 3. A second embodiment of a system illustrating the principles of the present invention is illustrated at 10A in FIGS. 2 and 4. Several components of the two systems 10, 10A are the same; in the following description and in FIGS. 1-4 the same reference numbers are used for the components of the systems that are the same.

Both of the first and second illustrated systems 10, 10A are illustrated for use in knee arthroplasty surgical procedures. In FIGS. 1-4, the systems 10, 10A are illustrated in use with a patient's leg 12. The patient's leg 12 has a knee joint 14, a proximal thigh portion 16 on the proximal side of the knee joint 14 and a distal portion 18 on the distal side of the knee joint 14. The patient's ankle 20 is on the distal side of the knee joint 14. It should be understood that although the illustrated embodiments are shown and described with respect to the knee joint and knee arthroplasty, the principles of the present invention may be applied to other joints and other types of arthroplasty as well. The invention is not limited to a knee joint stabilization and support system unless expressly called for in the claims.

The first and second illustrated surgical instrument support systems 10, 10A comprise the following main parts: a proximal base 22, a distal base 24, 24A, a support frame 26, a first arm 30, a second arm 32, a third arm 34, and a tensioning mechanism associated with each arm. The surgical instrument support systems 10, 10A may be comprise parts of surgical instrument systems that include surgical instruments such as resection guides 28 and accessories such as computer navigation trackers 400, 402, 404.

In the first and second illustrated embodiments, the proximal base 22 is sized and shaped to be mountable on the exterior of the patient's leg 12 on the proximal portion 16 on the proximal side of the knee joint 14 and the distal bases 24, 24A are both sized and shaped to be mountable on the exterior of the patient's leg 12 on the distal portion 18 on the distal side of the knee joint 14. In the illustrated embodiments, the resection guide 28 is selectively mountable to the support frame 26. As discussed in more detail below, either of the illustrated systems 10, 10A may be used with a plurality of resection guides. The first and second illustrated systems 10, 10A also include an inflatable proximal cuff 23 and a source of compressed air 25. The first illustrated system 10 includes an inflatable distal cuff 27 while the second illustrated system 10A includes an ankle clamp 29.

As described in more detail below, the tensioning mechanism associated with the arms 30, 32, 34 may comprise a plurality of actuators 41, 46, 52. The actuators 41, 46, 52 may be pneumatic, mechanical, electrical (for example, a solenoid transducer) or magnetic. The inflatable cuffs 23, 27 and actuators 41, 46, 52 may be connected to the source of compressed air 25 through switches 31, 33 operable by the surgeon so that the cuffs 23, 27 may be inflated simultaneously and so that the actuators 41, 46, 52 may be operated simultaneously to simultaneously increase the tension in the three tensioning mechanisms.

As shown in FIGS. 1 and 2, an additional resection guide 36 may be included with either system 10, 10A. Thus, the support portion (that is the portion that supports the resection guide) of either system 10, 10A can advantageously be used to support a plurality of different resection guides, so that the system can be used to prepare a bone for a variety of sizes of implant components, and can also be used to support resection guides that are to be used in resecting different bones: the support system of either system 10, 10A can be repositioned intraoperatively so that the same support system can be used to perform resections of the proximal tibia, the distal femur and the patella during knee arthroplasty.

The first support arm 30 of each of the illustrated systems 10, 10A has a first end 38 and a second end 40. The first end 38 is connected to the support frame 26 and the second end 40 of the first and second illustrated embodiments is connected to the proximal base 22 through a first actuator 41. The second support arm 32 of each of the illustrated systems 10, 10A also has a first end 42 and a second end 44. The first end 42 is connected to the support frame 26 at a position spaced from the connection of the first end 38 of the first support arm 30 to the support frame. The second end 44 of the second support arm 32 in the first and second illustrated embodiments is connected to the proximal base 22 through a second actuator 46. The third support arm 34 also has a first end 48 and a second end 50. The first end 48 of the third support arm 34 is connected to the support frame 26 at a position spaced from both the connection of the first end 38 of the first support arm 30 and the second end 44 of the second support arm 32 to the support frame 26. In the first and second illustrated embodiments, the connections of the first ends 38, 42, 48 of the support arms 30, 32, 34 to the support frame 26 are evenly spaced about the support frame 26 (about 120° apart for the circular support frame illustrated in FIGS. 1 and 2). The second end 50 of the third support arm 34 of the first and second illustrated embodiments is connected to the distal base 24 (or 24A) through a third actuator 52.

To allow for use of the system with a variety of patient anatomies, each arm 30, 32, 34 may have a length of 30-45 cm. or about 12-18 inches. It should be understood that it may be desirable for the distal arm 34 to have a greater length than the proximal arms 30, 32. It should also be understood that these dimensions are provided for illustrative purposes only; the invention is not limited to any particular dimension unless expressly called for in the claims.

All three support arms 30, 32, 34 comprise similar parts described below with respect to FIGS. 8 and 9. Although described with respect to the first arm 30, it should be understood that the following description applies to all three support arms 30, 32, 34. Each support arm 30, 32, 34 comprises a series of articulatable linkages defined by a plurality of ball and socket members slidably strung along a tension member 57 (shown in FIG. 8 and at 57A in FIG. 9).

Figure 8:
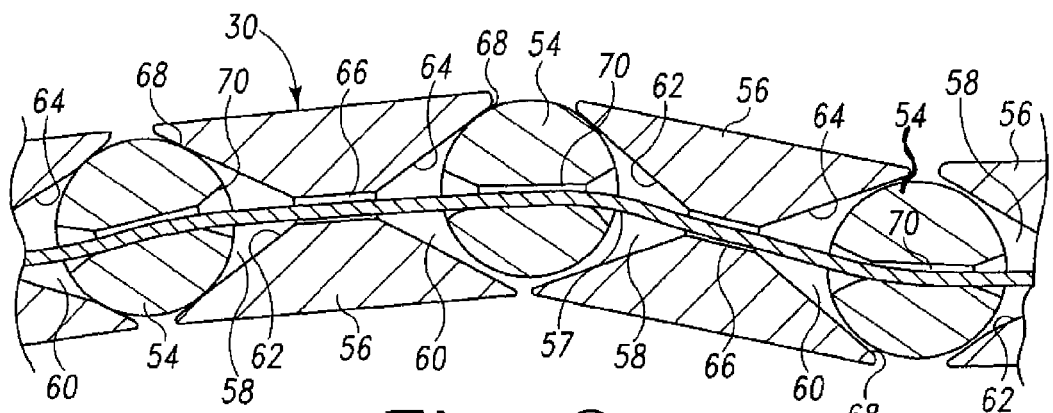
FIG. 8 is a longitudinal cross-section of an exemplary ball and socket structure that may be used for any or all of the three arms of the systems shown in FIGS. 1 and 2.

In the embodiment of FIG. 8, the arm 30 comprises a series of discrete ball members 54 and socket members 56. Each socket member 56 in the embodiment of FIG. 8 comprises a generally cylindrical member with generally conical openings 58, 60 defined by tapered surfaces 62, 64 at each end. The conical openings 58, 60 are connected by a cylindrical through-bore 66. Portions of one ball member 54 are received within each conical opening. The outer surface 68 of the portion of the ball member 54 received in each conical opening 58, 60 frictionally engages the tapered surfaces 62, 64 of the socket member 56. Each ball member 54 has a through-bore 70 and may have tapered lead-in surfaces. The arm 30 illustrated in FIG. 8 comprises a plurality of alternating ball members 54 and socket members 56. The tensioning member 57 comprises a cable that extends through the bores 70 of the ball members 54, through portions of the conical end openings 58, 60 and through-bore 66 of the socket members 56 so that the alternating ball and socket members 54, 56 are slidably strung along the cable 57 to form the articulating linkages. Tension in the cable 57 maintains frictional engagement between the adjacent ball and socket members 54, 56.

Figure 9:
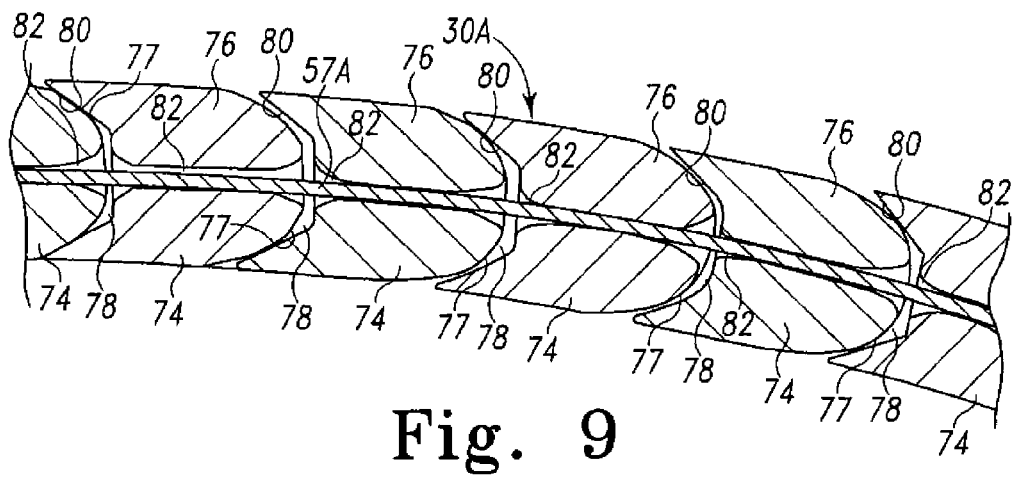
FIG. 9 is a longitudinal cross-section of an alternative ball and socket structure that may be used for any or all of the three arms of the systems shown in FIGS. 1 and 2.

In the arm illustrated in FIG. 9, designated 30A, the ball and socket members comprise a series of unitary structures 74, each having a substantially hemispherical-shaped end 76 with a curved outer surface 77 and a generally frusto-conical-shaped opening 78 defined by tapered walls 80 at the opposite end. A through-bore 82 extends longitudinally through each unitary structure 74. A cable 57A extends through the through-bore 82 and plurality of unitary ball and socket structures 74 are slidably strung along the cable 57A in series. The cable 57A is in tension to maintain frictional engagement between the adjacent unitary ball and socket structures 74.

In the arms 30, 30A illustrated in both FIGS. 8 and 9, the tension maintained in the cable 57, 57A defines the stiffness of the articulating joints defined by the ball and socket members 54, 56, 74. Increasing the tension by shortening the cable 57, 57A of each arm 30, 30A brings the adjacent ball and socket members 54, 56, 74 into closer contact, increases the friction between the adjacent elements 54, 56, 74, and thereby increases the stiffness of the articulating joints of the arm 30, 30A. Thus, by adjusting the tension in the cable 57, 57A (or the length of cable 57, 57A extending through the adjacent ball and socket members 54, 56, 74), the relative stiffness or rigidity of the supporting arm 30, 30A can be varied.

To control the relative stiffness or rigidity of each of the supporting arms 30, 32, 34, one end of each cable 57 is fixed at the support frame 26 and the other end of each cable 57 extends into the actuator 41, 46, 52 associated with that arm 30, 32, 34. By activation of the actuators 41, 46, 52, short lengths of cable 57 can be pulled into each actuator 41, 46, 52 to shorten and increase the tension in the cable 57, thereby stiffening the arms 30, 32, 34. Releasing the actuators 41, 46, 52 deceases the tension in the cables 57 and loosens the arms 30, 32, 34. Thus, when the three arms 30, 32, 34 are in the relaxed or more flexible state (that is, when the actuators 41, 46, 52 are in the released position), the surgeon can move the support frame 26 into a desired position, alignment and orientation and then activate the actuators 41, 46, 52 to stiffen the arms 30, 32, 34 to substantially lock the support frame 26 in that desired position, alignment and orientation.

It will be appreciated that each ball and socket joint in each support arm can pivot about multiple axes so that the three support arms 30, 32, 34 allow for movement of the support frame 26 in more than three degrees of freedom when the actuators 41, 46, 52 are in the released position. Since, as described below, the support frame 26 carries and supports the resection guide 28, 36, the system of the present invention allows the surgeon to set the position, alignment and orientation of the resection guide 28, 36 in more than three degrees of freedom and to substantially lock the resection guide 28, 36 in the desired position, alignment and orientation. And since, as described below, the support frame 26 is capable of supporting different resection guides 28, 36, the system of the present invention can be used to set the position, alignment and orientation of multiple resection guides 28, 36 to make multiple resections accurately, simply and efficiently. All or substantially all of the needed resections for total knee arthroplasty can be accomplished using multiple resection guides 28, 36 and the support system of the present invention.

It will be appreciated that the stiffness of each arm 30, 32, 34 will depend upon factors such as the sizes of the ball and socket members 54, 56, 74, the angles of the tapered surfaces 62, 64, 80 defining the conical and frusto-conical openings 58, 60, 78, the surface finishes of contacting surfaces 62, 64, 68, 80 of adjacent elements 54, 56, 74 and the materials used to make the ball and socket members 54, 56, 74. For the embodiment of FIG. 8, the ball structures 54 can be made of a different material than the socket structures 56; for example, the ball structures 54 can be made of a resilient material, such as polyethylene for example, and the socket structures 56 can be made of a non-resilient material, such as stainless steel or aluminum for example. With such resilient and non-resilient materials used, increasing cable tension should cause the resilient balls 54 to deform against the non-resilient sockets to increase the surface area in contact between the adjacent components 54, 56. It is expected that various metals, polymers, copolymers and composites may be used for the ball and socket members. It may be desirable to make the ball and socket members out of radiolucent materials. A heat resistant thermoplastic such as RADEL.RTM. polyarylethersulfone (PAES) may be used since it is understood to be sterilizable in a steam autoclave. RADELL® PAES is understood to be available from Amoco Polymers, Inc. of Alpharetta, Ga., and from suppliers such as Piedmont Plastics, Inc. of Charlotte, N.C. At least some commercially available acetal copolymers are expected to be usable, such as DELRIN® material available from E.I. DuPont de Nemours and Co. of Wilmington, Del. and CELCON® polyoxymethylene available from Celanese Corporation through Ticona-US of Summit, N.J. The cable 57, 57A can comprise, for example, a braided stainless steel or polymer (e.g. nylon) cable. Generally, any material suitable for use for surgical instruments and having characteristics suitable for the application can be used for the ball and socket members 54, 56, 74 and cable 57, 57A; the invention is not limited to any particular material unless expressly called for in the claims.

Two examples of suitable actuators 41, 46, 52 are illustrated in the accompanying drawings. For simplicity, one actuator 41 of the three actuators provided in the system will be described below; it should be understood that the following description applied to all three actuators 41, 46, 52 that are provided in each system.

Figure 10:
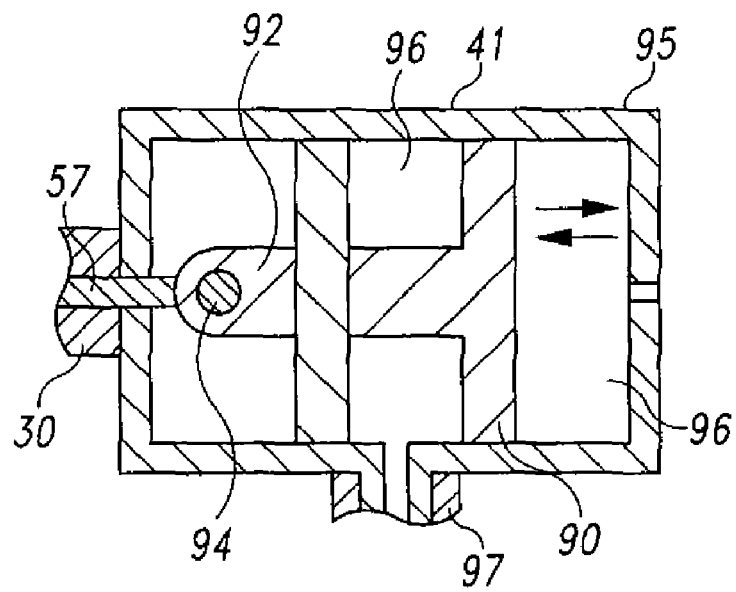
FIG. 10 is a cross-section of an exemplary pneumatic actuator that may be used with the arms of the systems of either FIG. 1 or FIG. 2, shown with the actuator in a unactivated position associated with a more flexible state of the arms of the system.
Figure 11:
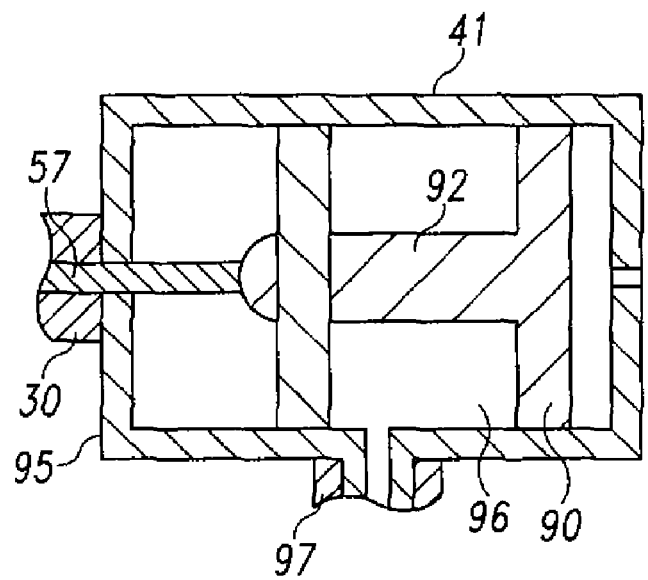
FIG. 11 is a cross-section similar to FIG. 10, shown with the actuator in an activated position associated with a more rigid state of the arms of the system.

A first example of a suitable actuator 41, shown in cross-section in FIGS. 10-11, is a pneumatic actuator with an internal piston 90 connected to an extension member 92 that is connected to an end 94 of the cable 57 within a housing 95. The position of the piston 90 and cable end 94 when the actuator is in the released state is shown in FIG. 10. When compressed air enters chamber 96 through hose 97, the piston 90 moves, pulling the cable 57 into the actuator housing 95 to increase the tension in the cable 57, as shown in FIG. 11. As shown in FIG. 1, a single source 25 of compressed air may be connected to supply all three actuators 41, 46, 52 through the switch mechanism 33 so that all three pistons will be moved simultaneously to simultaneously increase the stiffness of all three support arms 30, 32, 34 to thereby stabilize and substantially lock the position, alignment and orientation of the support frame 26.

Figure 12:
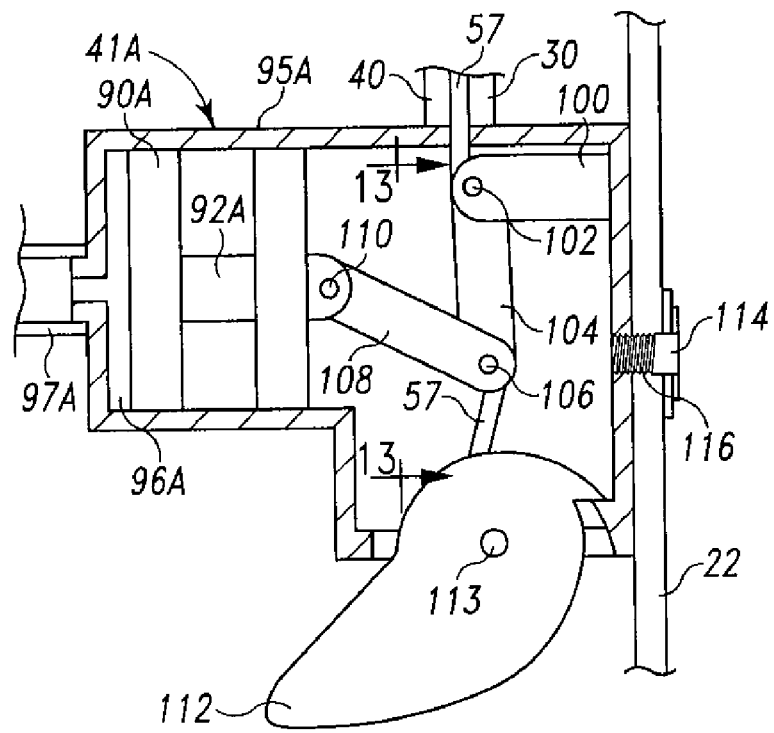
FIG. 12 is a cross-section of a second exemplary pneumatic actuator with a manual override option, shown with both the pneumatic and manual options of the actuator in unactivated positions associated with a more flexible state of the arms of the system.
Figure 13:
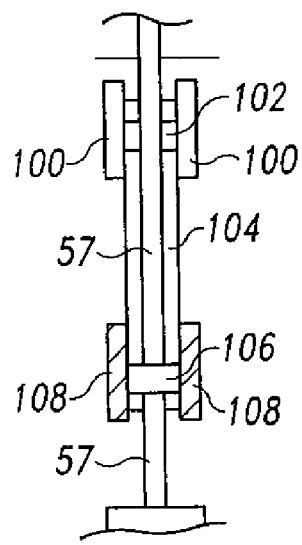
FIG. 13 is a cross-section taken along line 13-13 of FIG. 12, showing the articulating linkage within the actuator.

A second example of a suitable actuator 41A is illustrated in FIGS. 12-15. In the second example, each actuator 41A is operable pneumatically as in the first embodiment, but also includes a manual override in case of failure of the pneumatic system. Thus, the second example includes an internal piston 90A connected to an extension member 92A within a housing 95A. A source of compressed air may be connected through a suitable hose 97A and switch mechanism 33 to supply air to inner chamber 96A for selectively moving the piston 90A. The second example also includes an internal linkage mechanism comprising a pair of link members 100 fixed to the interior of the housing 95A. This pair of fixed link members 100 is pivotally connected through a pin 102 to a second link member 104. The second link member 104 is pivotally connected through a pin 106 to a pair of third link members 108. The pair of third link members 108 is pivotally connected through a pin 110 to the piston extension member 92A. As shown in FIG. 13, the cable 57 extends over one side of the pin 102 and then over the opposite side of the pin 106. The cable 57 then connects eccentrically to a manually-operable lever 112 (see FIGS. 12 and 14-15). The manually-operable lever 112 is pivotally connected to the actuator housing 95A through a pin 113.

Figure 14:
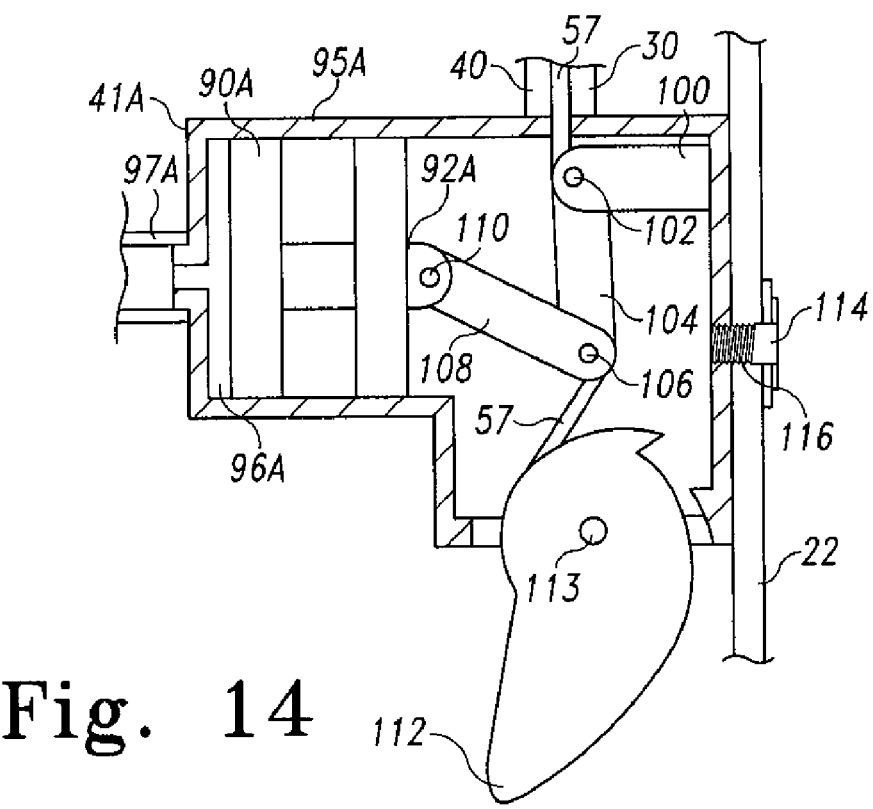
FIG. 14 is a cross-section similar to FIGS. 12 and 13, showing the actuator with the manual lever activated to increase the rigidity of the arm while the pneumatic piston is unactivated.
Figure 15:
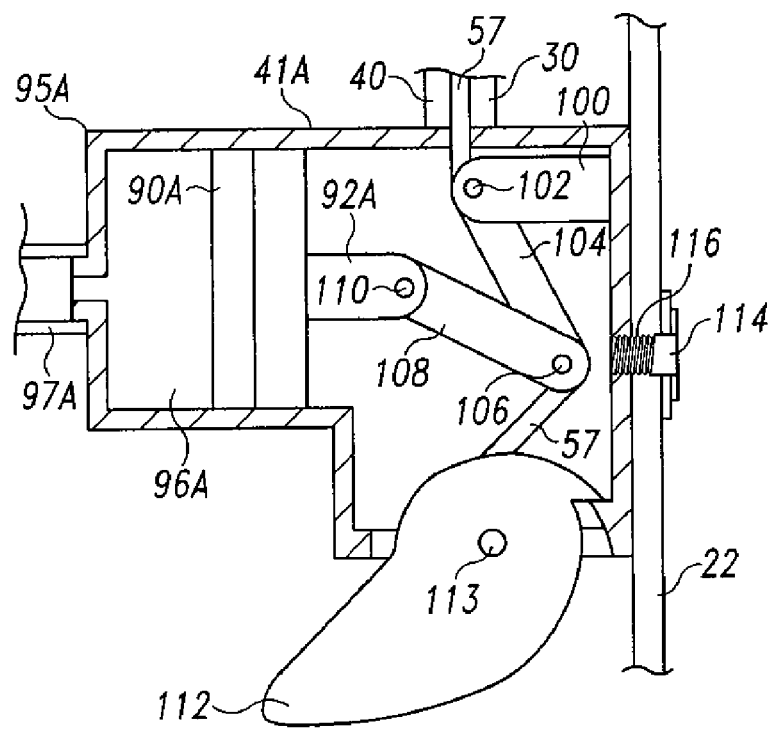
FIG. 15 is a cross-section similar to FIG. 12, showing the actuator with the pneumatic piston activated to increase the rigidity of the arm while the manual lever is unactivated.

FIG. 12 illustrates the actuator 41A in a released state. FIG. 14 illustrates manual operation of the actuator 41A: the exposed end of the lever 112 is pivoted from the position shown in FIG. 12 to the position shown in FIG. 14, thereby pulling the cable 57 into the housing 95A to stiffen the arm 30. The actuator 41A may include a locking mechanism (not shown) for temporarily locking the lever 112 in the position shown in FIG. 14. When the lever 112 is moved back to the position shown in FIG. 12, a length of the cable 57 is released to increase the flexibility of the arm 30. FIG. 15 illustrates pneumatic operation of the actuator 41A: when the switch 33 (shown in FIG. 1) is actuated, compressed air flows through the line 97A into the chamber 96A of the actuator 41A, pushing the piston 90A and the extension member 92A to the right, thereby forcing pin 106 connecting the link members 104, 108 to the right to pull the cable 57 into the housing 95A to stiffen the arm 30. When the pneumatic pressure in chamber 96A is released, the piston 90A, extension member 92A, link members 104, 108 and pin 106 return to the position shown in FIG. 12, thereby releasing a length of the cable 57.

It will be appreciated that the pneumatic actuators may include suitable valves (not shown) for operation as described above.

It will also be appreciated that other types of actuators could be used. For example, a solenoid or magnetic transducer or a solenoid or magnetic transducer with a mechanical override option could be used for the actuators 41, 41A, 46, 52. In addition, as described in more detail below, the actuators could be positioned and connected to act upon the end of the cable 57 at the first ends 38, 42, 48 of the arms 30, 32, 34 instead of upon the seconds ends 40, 44, 50. It is anticipated that commercially available pneumatic piston devices, mechanical switches and solenoid or magnetic transducers can be used for the actuators, or that such commercially available devices can be readily modified to meet the needs of the present application. In addition, the mechanical override option could be achieved by providing two cables extending through the balls and sockets of each arm; one cable of one arm could be connected to one type of actuator and the other cable of that arm could be connected to another type of actuator.

FIGS. 12 and 14-15 also illustrate one means of connecting the actuator 41A to the proximal base 22. As there illustrated, a screw 114 extends through a hole in the base 22 and into a mating threaded hole 116 in the housing 95A. It should be appreciated that there are several ways in which the actuators 41, 41A, 46, 52 could be connected to the bases 22, 24. In addition to mechanical connection through screws, the actuators could be connected to the bases 22, 24 through mechanical clamps, bolts, snaps, snap fits or interference fits, through provision of complementary mounting structures or through adhesives, for example.

Figure 6:
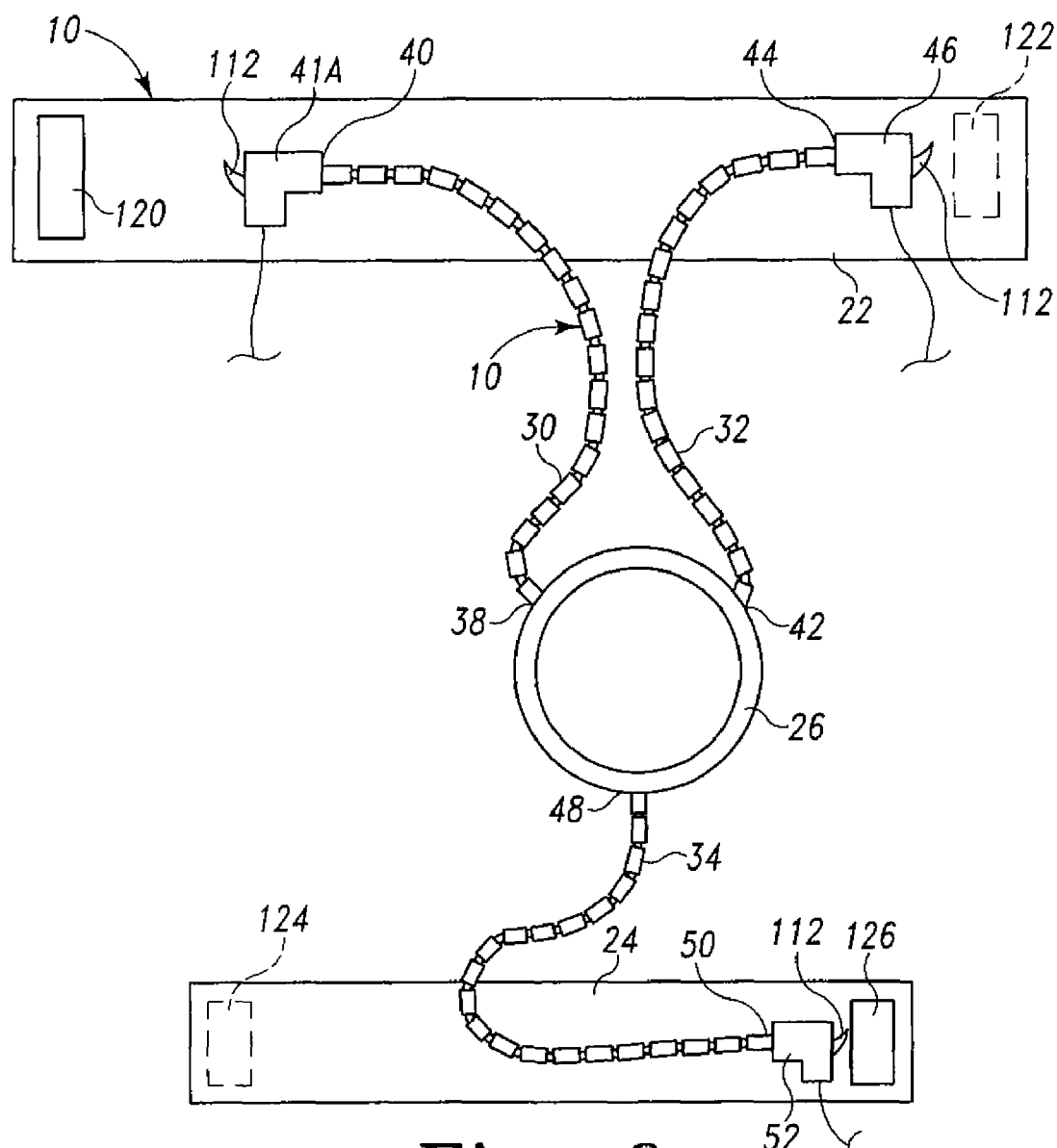
FIG. 6 is a top plan view of the surgical instrument support system of FIG. 1 before mounting on the patient's leg and with the proximal and distal bases shown in an unwrapped state.

An example of a proximal base 22 is illustrated in FIG. 6. The illustrated proximal base 22 comprises an elongate belt or strap of flexible, inelastic material. The belt or strap of material is sized so that it can be wrapped transversely around the proximal portion 16 of the patient's limb, and preferably is sized so that it can be wrapped around the inflatable proximal cuff 23. A belt or strap having a length of 75-90 cm (about 30-36) inches and a width of about 10-15 cm (about 4-6 inches) should be acceptable for this purpose. The illustrated proximal base 22 includes hook and loop strips 120, 122 (such as Velcro™ brand fasteners) so that the base 22 can be fixed about the patient's limb. Although other mechanisms (such as buckles or snaps) could be used. The connections between the base 22 and the two actuators 41, 46 are spaced apart so that when the base is wrapped around the patient's limb, the actuators 41, 46 will be spaced apart and the second ends 40, 44 of the arms 30, 32 will be spaced apart (preferably diametrically opposed on the patient's proximal limb).

The distal base 24 of the embodiment of FIG. 1 is also illustrated in FIG. 6, and also comprises an elongate belt or strap of flexible material. The belt or strap of material is sized so that it can be wrapped transversely around the distal portion 18 of the patient's limb, and preferably is sized so that it can be wrapped around the inflatable distal cuff 27. A belt or strap having a length of about 30-40 cm. (or about 12-15 inches) and a width of about 10-15 cm. (or about 4-6 inches) should be acceptable. The illustrated distal base 24 includes hook and loop strips 124, 126 (such as Velcro™ brand fasteners) so that the elongate base 24 can be fixed about the patient's limb, although other mechanisms (such as buckles and snaps) could be used.

In the embodiment of FIG. 6, the second ends 40, 44 of the first and second arms 30, 32 are both connected to the first and second actuators 41A, 44 which are connected to the base 22 in the manner illustrated in FIGS. 12 and 14-15; the second end of the third arm 34 is connected to the third actuator 52 which is connected to the base 24 in the manner illustrated in FIGS. 12 and 14-15. In the embodiment of FIG. 6, all of the actuators 41A, 46, 52 are of the type illustrated in FIGS. 12 and 14-15. The third actuator 52 can be connected to the base 24 of FIGS. 1 and 6 with screws, as described above with respect to FIGS. 12 and 14-15.

The straps or belts comprising both bases 22, 24 of the embodiment of FIG. 1 and the proximal base 22 of FIG. 2 can be made of any suitable material for surgical applications. Suitable materials should be sterilizable, flexible enough to wrap around the patient's limb, substantially inelastic, and sturdy enough to support the actuators 41, 46, 52 and second ends 40, 44, 50 of the arms 30, 32, 34. For example, webs of nylon, polypropylene, polyester or other polymers may be suitable. The material may be reinforced, for example, with fibers or with stays (extending, for example, across with width or shorter dimension of the belt) and the strap or belt may have multiple plies for strength.

Figure 5:
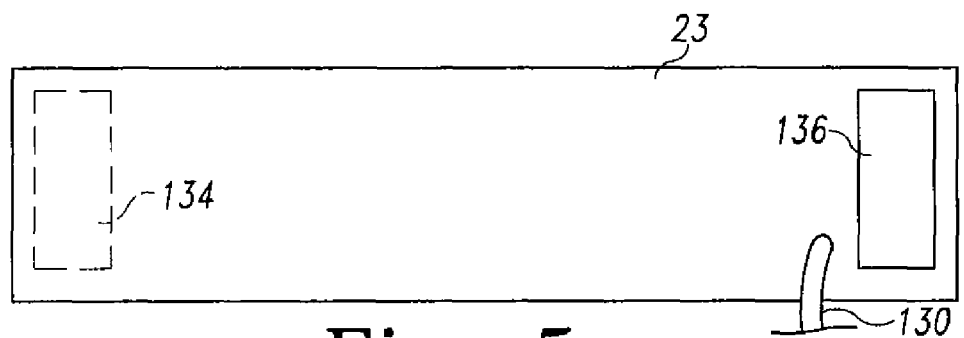
FIG. 5 is a top plan view of a proximal cuff used in the systems of FIGS. 1 and 2.
Figure 7:
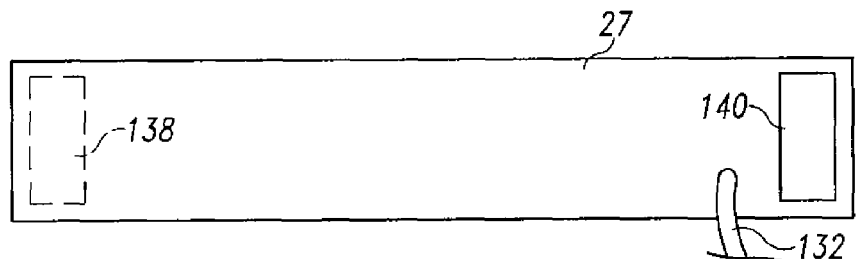
FIG. 7 is a top plan view of a distal cuff used in the system of FIG. 1.

In the embodiment of FIG. 1, the straps or belts comprising the bases 22, 24 overlie and surround the inflatable proximal cuff 23 and the inflatable distal cuff 27. Both inflatable cuffs 23, 27 can comprise standard air-tight bladders connected to air-supply hoses, such as those shown at 130 and 132 in FIGS. 5 and 7. For example, both cuffs 23, 27 can be made of materials and constructed similar to standard inflatable blood pressure cuffs. In the illustrated embodiments, both cuffs 23, 27 include hook and loop strips 134, 136, 138, 140 (such as Velcro™ brand fasteners) so that the cuffs 23, 27 can be fixed about the patient's limb, although other mechanisms (such as buckles or snaps) could be used. The proximal cuff 23 may be sized to extend transversely around the proximal portion 16 of the patient's limb 12 and the distal cuff may be sized to extend transversely around the distal portion 18 of the patient's limb 12. In the embodiment illustrated in FIG. 1, the proximal cuff 23 has a width slightly greater than the width of the proximal base strap or belt 22 and the distal cuff 27 has a width slightly greater than the width of the distal base strap or belt 24. For example, the proximal cuff could be about 75-90 cm (about 30-36) inches by about 10-15 cm (about 4-6 inches).

In the embodiment of FIG. 1, the air hoses 130, 132 leading to the cuffs 23, 27 are connected through the switch 31 to the source of compressed air 25. When the switch 31 is actuated, air is introduced to the hoses 130, 132 simultaneously, inflating the cuffs 23, 27 against the patient's limb and against the two base straps 22, 24. As the cuffs 23, 27 inflate, the positions of the two base straps 22, 24, actuators 41, 46, 52 and second ends 40, 44, 50 of the arms 30, 32, 34 are stabilized with respect to the patient's limb. In the embodiment of FIG. 2, only a proximal cuff 23 is included, and inflation of the cuff 23 stabilizes the positions of the proximal base strap 22, actuators 41, 46 and second ends 40, 44 of two of the arms 30, 32. It will be appreciated that suitable valves (not shown) may be used for operation of the bladders as described above.

Although the straps or belts defining the bases 22, 24 and the expandable cuffs 23, 27 may comprise discrete elements, it should be understood that each belt and cuff could comprise a unitary structure. It should also be understood that each cuff or combination base/cuff component could comprise other types of structures. One example of a suitable alternative structure is a vacuum immobilizer. A suitable vacuum immobilizer support base or combination cuff/base could comprise an elongate air-tight bag or casing of flexible material filled with elastically deformable spherulic beads made of a material such as expanded polystyrene. The bag or casing could include evacuation ports or valves through which air may be evacuated to form vacuums therein. Air would be evacuated after the bag or casing was wrapped around the patient's ankle or thigh; evacuation of air would cause the beads to compact together to form fit the patient's ankle or thigh and to become rigid in this shape. Examples of devices utilizing such structures include U.S. Pat. Nos. 6,308,353, 6,066,107 and U.S. Pat. No. 3,762,404, the disclosures of which are incorporated by reference herein in their entireties.

It should be understood that the materials and dimensions described above for the bases and cuffs are provided for illustrative purposes only. The invention is not limited to any particular material or dimension unless called for in the claims.

Figure 16:
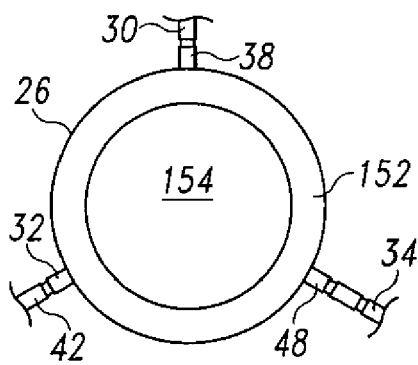
FIG. 16 is a top plan view of an exemplary support frame that may be used with the systems of FIGS. 1 and 2.
Figure 17:
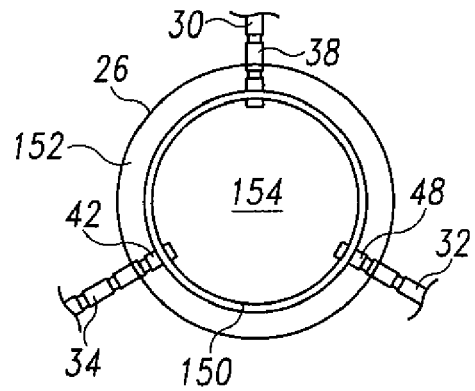
FIG. 17 is a bottom plan view of the support frame of FIG. 16.
Figure 18:
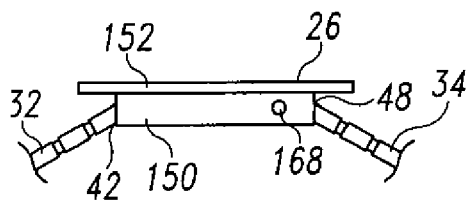
FIG. 18 is a side elevation of the support frame of FIGS. 16-17.

In both the first and second embodiments, a variety of structures can be used for the support frame 26 connected to the first ends 38, 42, 48 of the three arms 30, 32, 34. In a first embodiment of the support frame 26, illustrated in FIGS. 16-18. As there shown, the support frame 26 includes a hollow cylindrical body 150 and an annular top plate 152. In this embodiment, the first ends 38, 42, 48 of the arms 30, 32, 34 are connected to the cylindrical body 150 in any suitable manner. Preferably, the positions of the ends of the cables 57 at the first ends 38, 42, 48 are fixed with respect to the cylindrical body 150. The first ends 38, 42, 48 may be connected to the body 150 in any suitable manner, such as by adhesive, welding, by screws, bolts or any other standard method.

The hollow cylindrical body 150 and annular top plate 152 define an opening 154 comprising a surgical window. The diameter of the opening or window 154 is large enough so that at least one surgical implement, such as a resection guide, can be placed in the window for use by the surgeon. For example, the diameter may be 3-4 inches or about 7.5-10 cm. It should be understood that this dimension is provided for illustrative purposes only; the invention is not limited to any particular dimension unless expressly called for in the claims.

Figure 19:
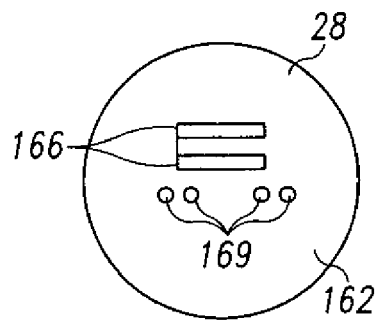
FIG. 19 is a top plan view of an exemplary resection guide that may be used with the support frame of FIGS. 16-18.
Figure 20:
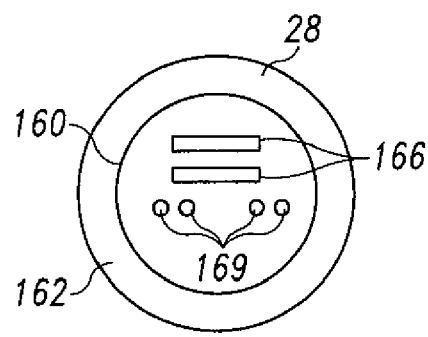
FIG. 20 is a bottom plan view of the resection guide of FIG. 19.
Figure 21:
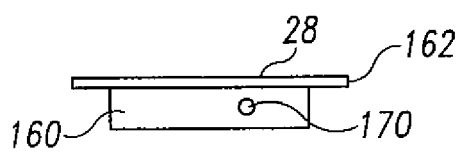
FIG. 21 is a side elevation of the resection guide of FIGS. 19-20.

An example of a resection guide that could be used with the first illustrated support frame 26 is illustrated in FIGS. 19-21. The first illustrated resection guide 26 comprises a solid cylindrical body 160 and a top plate 162. The solid cylindrical body 160 is sized and shaped to be received within and mate with the hollow cylindrical body 150 of the support frame. The top instrument plate 162 is sized and shaped to be supported by the annular top plate 152 of the support frame 26, and to extend substantially across the opening or window 154. The top instrument plate 162 and body 160 include one or more structures serving as resection guides. These structures can be parallel walls defining through-slots 166 to receive a saw blade (not shown). Alternatively, these structures can be walls defining a path for a surgical burr, as is shown in FIGS. 1 and 2 at 167 for the instrument 36. In either case, the slot 166 or path 167 extend through the top plate 162 and the entire cylindrical body 160 so that the cutting tool can reach the patient's bone surface. Pin-receiving holes 169 may be provided so that the cutting guide may be fixed to the patient's bone through the use of standard pins (not shown). It should be understood that the use of such pin-receiving holes and pins is optional; with the present invention, the resection guide may be supported by the instrument support system throughout the resection of the bones without fixing the resection guide to the patient's bone. The cylindrical bodies 150, 160 of the support frame 26 and resection guide 26 (or resection guide 36) may have transverse holes 168, 170 to receive a set screw (not shown) to prevent relative rotation between the support frame 26 and the resection guide 28.

The resection guides 28, 36 of the types illustrated in FIGS. 1-2 and 19-21 may be unitary and made of standard instrument materials or may be assemblies of multiple standard instrument materials. For example, the entire resection guide 28, 36 could be made of standard metals such as stainless steel or a significant portion of the resection guides 28, 36 could be made of a lighter weight material, such as a polymer, with metal inserts defining the cutting guide slot 166 or path 167. It may be desirable to make at least a part of the resection guides out of radiotranslucent material as described above.

Figure 22:
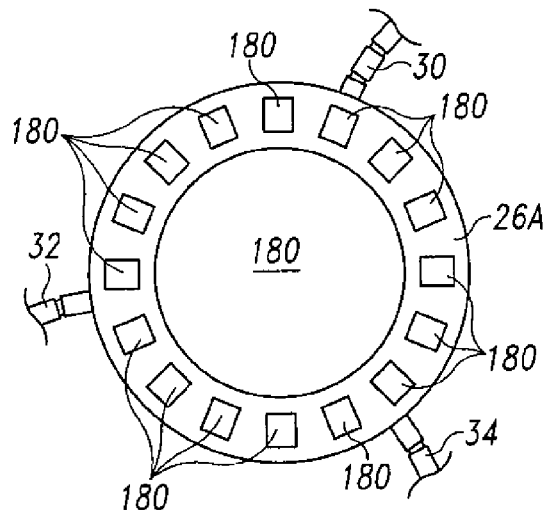
FIG. 22 is a top plan view of an alternative example of a support frame that may be used with the systems of FIGS. 1-2.
Figure 23:
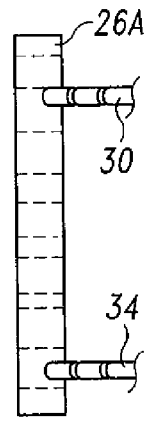
FIG. 23 is a side elevation of the support frame of FIG. 22.
Figure 24:
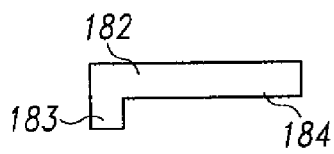
FIG. 24 is a side elevation of an exemplary mounting bar that may be used with the support frame of FIGS. 22-23.
Figure 27:
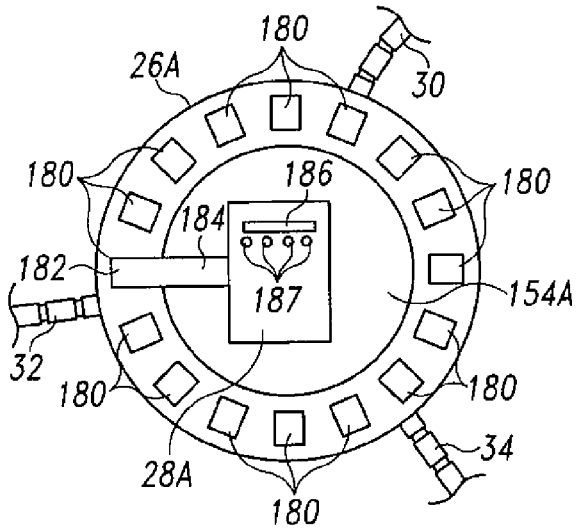
FIG. 27 is a top plan view of the resection guide of FIG. 26 assembled with the mounting bar of FIGS. 24-25 and mounted on the support frame of FIGS. 22-23 so that the resection guide is positioned in the operating window provided by the support frame.

A second example of a support frame is illustrated in FIGS. 22-23 and 27 at 26A. In this embodiment, the support frame 26A comprises an annular body with a plurality of spaced longitudinal through-holes 180 that are square in cross-section. The annular body defines an operating window 154A much like the operating window 154 of the embodiment of FIGS. 16-17. Arms 30, 32, 34 may be connected to the support frame 26A as in the first and second illustrated embodiments. An instrument system utilizing this support frame 26A could include a mounting bar 182 such as that shown in FIGS. 24 and 25, with a base 183 that is sized and shaped to be received in a complementary manner in the through-holes 180 of the support frame 26A and an arm 184 extending perpendicularly from the base 183. When the mounting bar 182 is mounted on the support frame, the arm 184 extends into the space above the operating window 154A. The base 183 and arm 184 of the illustrated mounting bar 182 are both square in cross-section. A resection guide may be provided, such as that shown at 28A with through-slots 186 sized, shaped and positioned to receive a cutting implement, such as a saw blade. The resection guide 28A may include a mounting bore such as that shown at 188 that is square in cross-section and sized to receive the arm 184 of the mounting bar 182 in a complementary manner. The resection guide 28A may also include pin-receiving holes 187 to receive standard pins (not shown) to mount the resection guide to the patient's bone. FIG. 27 illustrates the resection guide 28A assembled with the mounting bar 182 and the support frame 26A.

Figure 26:
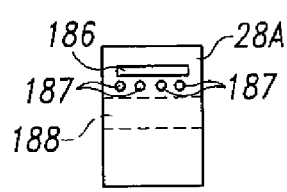
FIG. 26 is a top plan view of an exemplary resection guide that may be used with the mounting bar of FIGS. 23-25.

Another alternative support frame is illustrated in FIG. 28 at 26B. In this embodiment, the support frame 26B comprises a U-shaped body 190 defining a rectangular operating window 154B. Arms 30, 32, 34 may be connected to portions of the body 190 of the support frame 26B as in the first and second illustrated embodiments. A fourth arm 192 is provided in this embodiment. The fourth arm 192 is connected to a portion of the body 190 of the support frame 26B in the same manner as the first three arms, and has the same construction as that described above for the first three arms. The fourth arm 192 may be connected at its opposite end to the distal base 24 so that two arms 30, 32 are connected to the proximal base 22 and two arms 34, 192 are connected to the distal base 24. An instrument system utilizing this support frame 26B could include a mounting clamp 194 such as that shown in FIG. 30. Such a clamp could be clamped to the upper plate 196 of the body 190 of the support frame 26B. The illustrated mounting clamp 194 includes an arm 198 extending outward. When the clamp 194 is mounted on the support frame 26B, the arm 198 may extend over the operating window 154B. The arm 198 can be used to mount a resection block to the clamp, such as the resection block shown in FIG. 26 at 28A. When the resection guide 28A is so mounted, it will be positioned over the operating window 154B. Alternatively or additionally, a resection guide could be provided with a rectangular body shaped to be complementary with the shape of the three sides of the support frame 26B. Such a resection guide is shown at 200 in FIG. 31; the resection guide may have a rim to rest upon and be supported by the support frame 26B and one or more set screws may be provided to lock the resection guide 200 to the frame 26B. The resection guide 200 may have through-slots 202 sized, shaped and positioned to receive a cutting implement, such as a saw blade and may also or alternatively have through-openings defining a track 204 to receive a cutting instrument such as a burr. As in the case of the resection guide 28 of FIGS. 19-21, the resection guide 200 may be made of standard materials and may comprise a unitary structure or an assembly of components made of the same or different materials. It may also include pin-receiving holes 205 for mounting the resection guide to the patient's bone.

Figure 35:
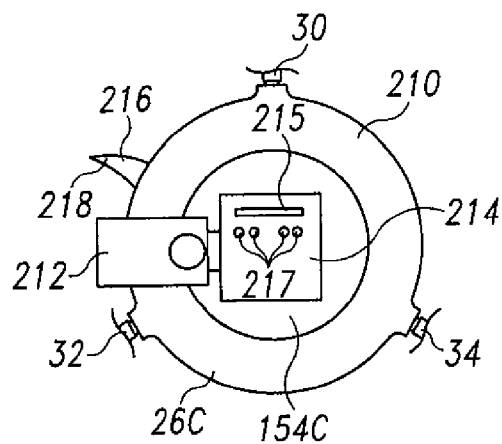
FIG. 35 is a top plan view of the support frame of FIGS. 32-34 shown assembled with a mounting clamp and resection guide so that the resection guide is supported in the operating window defined by the support frame.

A fourth example of a support frame 26C, illustrated in FIGS. 32-35, comprises a hollow annular body 210. Arms 30, 32, 34 may be connected to the body 210 of the support frame 26C as in the first and second illustrated embodiments, although as described in more detail below, the cables 57 would extend into the hollow interior of the body 210 of the support frame 26C. Clamps and resection guides could be used with such a support frame, as shown in FIG. 35 at 212 and 214 so that the resection guide 214 overlies the operating window 154C. Such a resection guide 214 may have a cutting guide slot 215 and pin-receiving holes 217. Alternatively, cylindrical resection guides with a top plate, as illustrated in FIGS. 1-2 and 19-21 at 28 and in FIGS. 1-2 at 36, could be used with such a support frame 26C.

Figure 25:
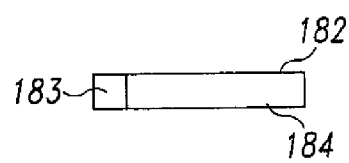
FIG. 25 is a bottom plan view of the mounting bar of FIG. 24.
Figure 32:
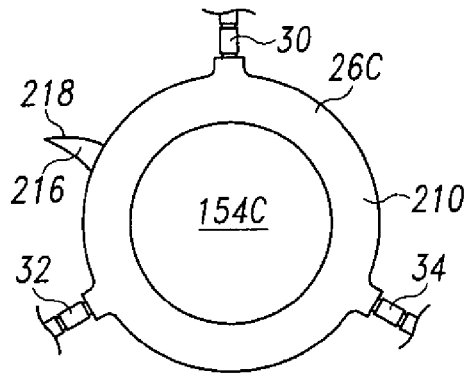
FIG. 32 is a top plan view of another alternative support frame that may be used in the systems of FIGS. 1 and 2.
Figure 34:
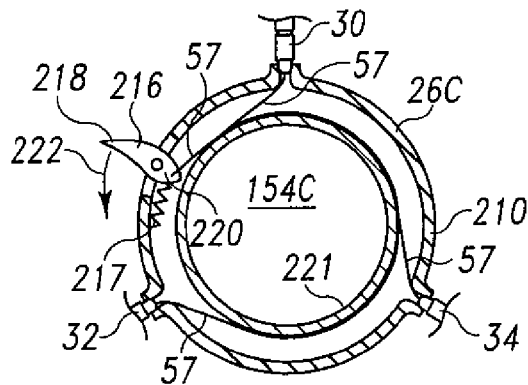
FIG. 34 is a cross-section of the support frame of FIGS. 32-33, taken along line 34-34 of FIG. 33.
Figure 33:
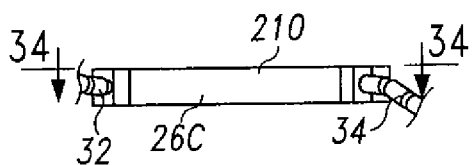
FIG. 33 is a side elevation of the support frame of FIG. 32.

The support frame 26C of FIGS. 32-25 includes a lever arm 216 pivotally mounted to the body 210 of the support frame 26C, with a portion 218 extending outward beyond the outer cylindrical periphery of the support frame 26C and a portion 220 within the hollow annular body 210 of the support frame 26C. In this embodiment, ends of all three of the cables 57 of the three arms 30, 32, 34 extend into the hollow interior of the body 210, wind around an inner cylindrical core 221 and connect to the lever arm 216. In this embodiment, the lever arm 216 is usually biased by a spring 217 in a direction to maximize the tension on the cables 57 so that the arms 30, 32, 34 are usually in their most rigid state. To relax the arms 30, 32, 34 for movement of the support frame 26C, the lever arm 216 is pivoted in the direction shown by arrow 222, thereby loosening all three cables 57 with movement of the single lever arm 216. When the lever arm 216 is released, it pivots back to its original position, returning the arms 30, 32, 34 to their most rigid state. With the support frame 26C of this embodiment, the system need not utilize actuators at the second ends 40, 44, 50 of the arms 30, 32, 34, since the lever arm 216 operates as a single mechanical actuator for all three arms 30, 32, 34. Advantageously, the surgeon can grasp the body 210 and squeeze the exposed portion 218 of the lever arm 216 to relax the arms 30, 32, 34, move the support frame 26C into the desired position, alignment and orientation, and then release the body and lever arm 216, leaving the support frame 26C in the desired position, alignment and orientation.

Figure 36:
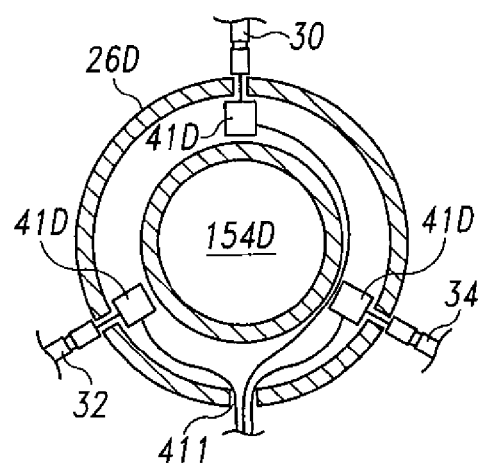
FIG. 36 is a cross-section similar to FIG. 34, showing an alternative set of actuators within the interior of support frame.

It will be appreciated that modifications can be made to the support frame 26C illustrated in FIGS. 32-25. For example, either a single or multiple pneumatic actuators of the type illustrated in FIGS. 10-11 (shown at 41D in FIG. 36) could be provided on the exterior or the interior of the hollow support frame body 410, as shown in FIG. 36. For interior mounted actuators, air hoses 97D (or electrical leads if a solenoid is used instead of a pneumatic actuator) could be fed through a port 411 in the support frame body 410.

All of the illustrated support frames 26, 26A, 26B, 26C may be made of standard materials for surgical instruments, such as metal (for example, stainless steel or aluminum). For a more lightweight design, it may be desirable to use non-metallic materials such as standard polymers and composites used in making surgical instruments. Polyarylethersulfone, acetal copolymer and polyoxymethylene may be appropriate radiotranslucent materials for the support frames. Although illustrated as unitary elements, the support frames could also comprise assemblies of the same or different materials.

In addition, all of the illustrated support frames 26, 26A, 26B, 26C may include features to allow other surgical implements to be supported by the support frame. For example, it may be desirable to allow for use of one or more components of the Codman® Greenberg Retractor and Handrest System or the Bookwalter Retractor kit (Codman & Shurtleff, Inc. of Rayhham, Mass.).

Figure 37:
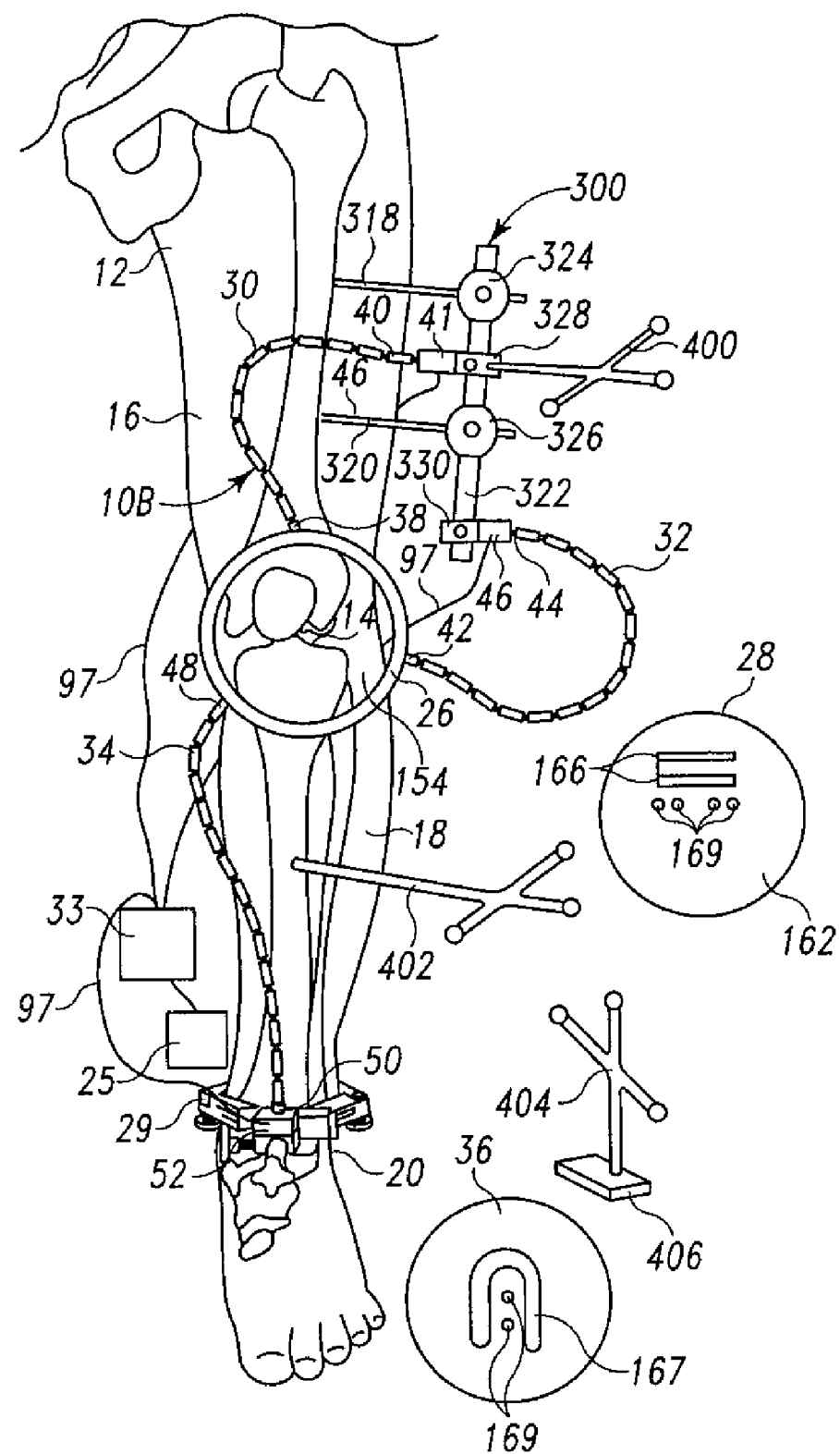
FIG. 37 is a view similar to FIG. 1, showing an alternative embodiment of a system with a different set of support structures for the arms and support frame.

Although the above-described embodiments of the system of the present invention are advantageous in that the bases and second ends of the arms 30, 32, 34 can be fixed in position without driving any support structures into the patient's bones, principles of these embodiments can be applied to other types of support structures as well. FIG. 37 illustrates such a system.

In the embodiment of FIG. 37, the instrument support system 10B includes an anchoring structure 300 that is mountable to a patient's bone to serve as the proximal base. The illustrated anchoring structure 300 comprises an assembly of a plurality of pins 318, 320, an anchoring bar 322, and a pair of anchoring clamp assemblies 324, 326 for fixing the anchoring bar 322 to the pins 318, 320. The pins 318, 320 may comprise standard surgical pins or wires used in orthopaedic surgery. The pins 318, 320 may be made of any standard surgical grade material such as stainless steel, and should have sufficient size and strength to support the weight of the arms 30, 32, 34 of the instrument system. For example, it is anticipated that stainless steel pins having a diameter of 5 mm. and an overall length of 20 cm. and with pointed ends should be usable. It should be understood that these materials and dimensions are provided as examples only; the present invention is not limited to any particular material or dimension unless expressly set forth in the claims.

The anchoring bar 322 of the anchoring structure 300 of the embodiment illustrated in FIG. 36 comprises a rod of any suitable surgical grade material, such as stainless steel. The bar 322 may be made of a material that can be sterilized by commercially available sterilization techniques without losing its strength. It may be desirable to make the anchoring bar out of a material that is radiolucent or radiotransparent so that radiographs may be taken intraoperatively without interference from the components of the anchoring structure 300. To decrease the overall weight of the system, it may be desirable to make the anchoring bar 322 out of a hollow tubular material such as stainless steel or out of a lightweight plastic material. For use in knee arthroplasty, the anchoring bar 322 may have a length of about 30 cm. and a diameter of about 18 mm., for example. The illustrated anchoring bar 322 is cylindrical in shape. It should be understood that these materials, dimensions and shape are provided as examples only; the present invention is not limited to any particular material, shape or dimension unless expressly set forth in the claims.

The anchoring bar 322 of the anchoring structure 300 of the embodiment illustrated in FIG. 37 is connected to the two pins 318, 320 through the two anchoring clamp assemblies 324, 326. The illustrated anchoring structure 300 also includes a pair of moveable clamp assemblies 328, 330. Each of the movable clamp assemblies 328, 330 are the same and each of the illustrated anchoring clamp assemblies 324, 326 are the same; these clamp assemblies 324, 326, 328, 330 are described in detail in U.S. patent application Ser. No. 11/260, 454 filed on Oct. 27, 2005 by Joseph G. Wyss and Mara C. Holm and entitled "SUPPORT FOR LOCATING INSTRUMENT GUIDES," which is incorporated by reference herein in its entirety. Use of the system described in U.S. patent application Ser. No. 11/259,987 filed on Oct. 27, 2005 by Joseph G. Wyss and Mara C. Holm and entitled "METHOD OF RESECTING BONE," which is also incorporated by reference herein in its entirety.

In the embodiment of FIG. 37, two of the arms 30, 32 are mounted on or connected to the two movable clamp assemblies 328, 330 through actuators 41, 46. The actuators 41, 46 may be mounted on or connected to the movable clamp assemblies 328, 330 by any suitable means, such as by screws, bolts, clamps, complementary mounting structures, adhesives or the like; alternatively, the actuators may be made as part of the movable clamp assemblies. The movable clamp assemblies 328, 330 are movable along the longitudinal axis of the anchoring bar 322 to a desired longitudinal position and then clamped to the bar 322 to fix the positions of the clamps 328, 330, and to thereby fix the positions of the second ends 40, 44 of the arms 30, 32.

Like the embodiment of FIG. 2, the embodiment illustrated in FIG. 37 uses an ankle clamp 29 to which the second end 50 of the third arm 34 is connected through an actuator 52. The illustrated ankle clamps are from the commercially available Specialist® 2 instruments (DePuy Orthopaedics, Inc., Warsaw, Ind.) for use with DePuy Orthopaedics' P.F.C.® Sigma Knee System. It should be understood that this ankle clamp is identified and illustrated for illustrative purposes only; the present invention could be used with other ankle clamps serving as the distal base 24. The actuator 52 can be fixed to the ankle claim 29 in any suitable manner, such as by screws, bolts, clamps, complementary mounting structures, adhesives or the like.

Advantageously, the instrument system of the present invention can be used in computer-assisted surgery. For such use, the embodiments illustrated in FIGS. 1, 2 and 37 include a plurality of computer navigation trackers 400, 402, 404. The illustrated computer navigation trackers 400, 402, 404 comprise emitters or reflector arrays. In FIGS. 1 and 2, two of the computer navigation trackers 400, 402 are attached directly to the patient's bones on both sides of the joint; in FIG. 37, one of the computer navigation trackers 402 is attached to the patient's tibia distal to the knee joint and the other computer navigation tracker 400 is attached to one of the movable clamps 328 on the proximal side of the knee joint. The instrument system may also include a computer navigation tracker, for example a third emitter or reflector array, such as that shown at 404 in FIGS. 1-2 and 37, for mounting to some part of the resection guide or cutting block 28: for example, the array 404 could be attached to or integral with a plate 406 that is sized and shaped to be received in a cutting guide slot 166 of the resection guide 28. It should be understood that other structures could be employed to attach an array to any of the illustrated resection guides 28, 36. The trackers 400, 402, 404 give the surgeon an image of the position, alignment and orientation of some known part of the instrument system, such as the guide slot 166 of the resection guide 28, with respect to the position, alignment and orientation of other landmarks, such as some part of the anchoring structure 200 or bone that is also displayed on a computer screen. The computer images can be used by the surgeon to guide the resection guide 26, 36 into a desired position, alignment and orientation while the arms 30, 32, 34 are in a less rigid state, and relatively easily movable; the surgeon can activate the actuators 41, 41A, 46, 52 with the resection guide 28, 36 in the desired position, alignment and orientation and to rigidify the arms 30, 32, 34 with the resection guide 28, 36 in this desired position, alignment and orientation. The surgeon may then perform the bone resections so that the bone may receive the prosthetic implant. An example of an emitter or reflector system potentially usable with the present invention is disclosed in U.S. Pat. No. 6,551,325, which is incorporated by reference herein in its entirety. The system of the present invention is expected to be particularly useful with the Ci™ computer assisted surgical system available from DePuy Orthopaedics, Inc. of Warsaw, Ind. However, any computer assisted surgery system, with appropriate emitters or sensors and computer with appropriate circuitry and programming could be used with the present invention.

The illustrated instrument systems could be used with alternative forms of computer navigation trackers for computer-assisted surgery. For example, instead of an array of emitters or reflectors that is attached to reference points, one or more computer navigation trackers could be embedded in the resection guide and patient's bone, as well as in the cutting instrument. For example, the computer navigation trackers could comprise electromagnetic sensors, such as one or more coils, transducers and transmitters appropriately housed and sealed, and the instrument system could include electromagnetic field generator coils, receiving antenna and computer with appropriate signal receiver and demodulation circuitry. Such systems are commonly referred to as "emat" (electromagnetic acoustic transducer) systems.

Although the present invention provides advantages in computer-assisted surgery, its use is not limited to computer-assisted surgery. Standard surgical instruments may be used to determine the appropriate position, alignment and orientation of the resection guide, such as a stylus or an extramedullary or intramedullary alignment rod.

It may be advantageous to provide some additional fine tuning of the position, alignment and orientation of the resection guide 28, 36 supported by the support frame 26. A finely adjustable resection guide is disclosed in U.S. patent application Ser. No. 11/410,404 filed on Apr. 25, 2006 by Diane L. Bihary and Troy D. Martin entitled "FINELY ADJUSTABLE RESECTION ASSEMBLY," which is incorporated by reference herein in its entirety. The resection assembly disclosed in that patent application may be mounted to one of the illustrated support frames 26 to allow for fine adjustment of the position, alignment and orientation of the resection guide with respect to the support frame. The resection assembly disclosed in that patent application may also be modified to facilitate mounting to one of the illustrated support frames through use of structures such as those shown in FIGS. 24-25 and 30. Moreover, the principles of the invention disclosed in that patent application may be applied to the design of resection guide of the type shown in FIGS. 19-21 and 31 so that these resection guides comprise assemblies of components that are finely adjustable with respect to the support frame.

The principles of the present invention could also be applied to other forms of resection guides for resection of other bones. For example, the system could be applied in setting the position and orientation of an ankle cutting block, an elbow cutting block, or a proximal femoral cutting block.

It will be appreciated that the system of the present invention is advantageous in that the same instrument support system 10, 10A, 10B can be used to position, alignment and orient cutting blocks for use in all bones of a joint. The surgeon need only change the resection guide and reposition the support frame 26 without moving either base.

Figure 4:
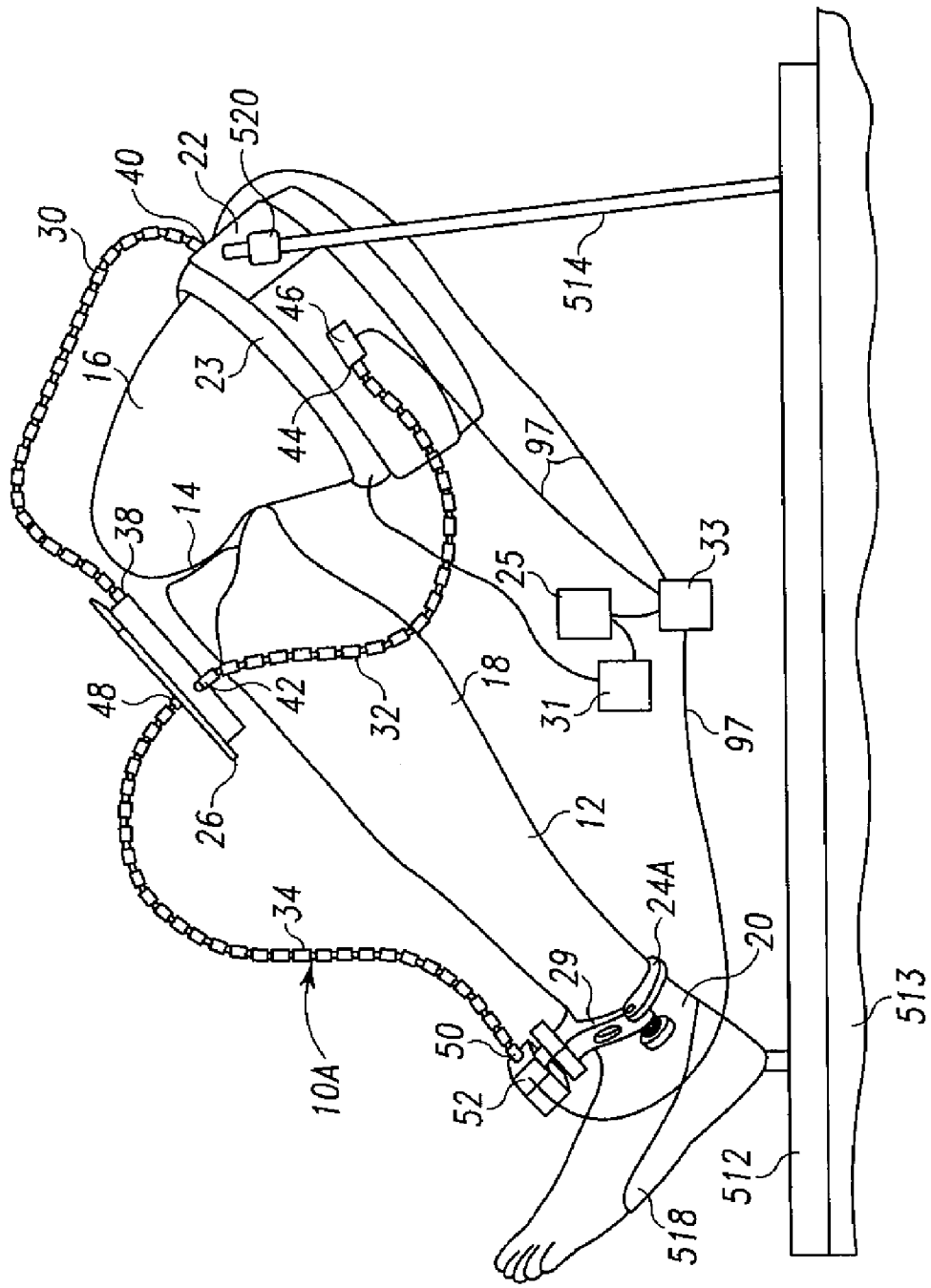
FIG. 4 is an elevation, from the lateral side of the patient's leg showing the patient's leg in flexion with the surgical instrument support system of FIG. 1 mounted on the patient's leg, the system being shown with an alternative set of actuators and with a system for fixing and stabilizing the position of the patient's leg.

The system of the present invention can be used advantageously with other surgical systems. FIGS. 3 and 4 illustrate the system of the present invention used in conjunction with the limb stabilizing system described in U.S. patent application Ser. No. 11/926,844 filed concurrently herewith by Carl F. Livorsi and entitled "LIMB STABILIZING SYSTEM FOR ARTHROPLASTY," the disclosure of which is incorporated by reference herein in its entirety. As shown in FIGS. 3 and 4, the illustrated stabilizing system includes a platform 512 clamped or otherwise temporarily fixed to the operating table 513, an outrigger 514 pivotally mounted to the platform 512 and a foot brace 518 slidably mounted to the platform 512. The foot brace 518 is placed on the patient's foot and the leg is flexed to the desired position by sliding the brace in a track (not shown) in the platform 512. When the patient's leg is at the desired degree of flexion, the outrigger 514 is pivoted up from the platform until it is alongside the proximal support base 22 on the patient's thigh. The outrigger 514 is then temporarily fixed to the proximal support base through a fixing mechanism, such as a hook and loop strip secured to the base 22 (such as Velcro™ brand fasteners). Locking mechanisms are then activated to temporarily fix the longitudinal position of the foot brace and the angular orientation of the outrigger 514, thereby stabilizing the position and angular orientation of the leg at a desired degree of flexion for performing resection of the patient's bones.

To use the system of the present invention, the patient is placed supine on the operating table and given a satisfactory anesthetic. The leg or other limb is prepped and draped in the usual fashion. For the system 10 of FIG. 1, the cuffs 23, 27 are placed around the thigh 16 and near the ankle 20. The bases 22, 24 are then wrapped around the cuffs 23, 27. The surgeon may then activate the switch 31 (which may comprise, for example, a floor pedal) to inflate the cuffs 23, 27. When the cuffs inflate, the positions of the bases 22, 24 are firmly secured on the patient's leg. For the system 10A of FIG. 2, the cuff 23 is placed around the thigh and the ankle clamp 29 is placed around the patient's ankle and the base 22 is wrapped around the proximal cuff 23 and then the cuff is inflated to firmly secure the proximal base to the patient's thigh.

Once the bases are firmly secured, the surgeon may then manually manipulate the support frame 26 while the arms 30, 32, 34 are in the more flexible state. The support frame 26 may be positioned as desired over the general area and then more finely positioned, aligned and oriented using conventional methods. As the support frame is moved, the shapes of the arms change accordingly. For example, in setting the tibial resection guide, since the support frame has more than three degrees of freedom of movement, the proximal-distal position, varus-valgus orientation and anterior-posterior slope of the resection guide may all be set simultaneously by moving the support frame to the location where the cutting guide slots provide the proper proximal-distal position, varus-valgus orientation and anterior-posterior slope.

If the procedure includes the use of a computer to position, align and orient the resection guide 28, computer navigation tracker 404 can be mounted to the resection guide 28 by sliding the plate 406 into the cutting guide slot (such as slot 166) of the guide structure 28; alternatively, a computer navigation tracker could be embedded within the guide structure 28. Other computer navigation trackers 400, 402 may be affixed to anatomical landmarks (or embedded within the patient's bone) or to one of the bases 22, 24 to serve as references or benchmarks for determining the relative position, alignment and orientation of the guide structure 28.

With or without computer guidance, the surgeon can then move the guide structure 28 into a desired position, alignment and orientation and then actuate switch 33 (which may, for example, comprise a foot pedal) to simultaneously actuate the three arm actuators 41 (or 41A), 46, 52 to tighten the cable 57 of each arm 30, 32, 34 simultaneously to rigidify the three arms 30, 32, 34 in the shape they have assumed. If a finely adjustable guide structure is used, the surgeon may make any necessary adjustments after the arms 30, 32, 34 have been stiffened.

If the surgeon is satisfied with the final fixed position, alignment and orientation and of the guide structure 28, the surgeon can place pins through the receiving holes 169, 187, 205, 217 in the guide structure and into the underlying bone (if the guide structure comprises a resection guide). Optionally, the surgeon may disengage the resection guide from the support frame after setting the pins. Throughout this process, the surgeon can monitor the position, alignment and orientation of the guide structure 28 on a monitoring device such as a computer screen. The computer navigation tracker 404 can be removed from the guide structure 28 once the surgeon is satisfied with its location.

It will be appreciated that at any time prior to setting pins through the guide structure, if the surgeon is dissatisfied with the location of the guide structure 28, switch 33 can be deactivated to release the actuators so that the arms 30, 32, 34 are once again more flexible. The support frame and resection guide can then be repositioned and the actuators activated again to rigidify the arms 30, 32, 34.

As set forth earlier, the surgeon need not affix the resection guide to the patient's bone. The resections can optionally be performed with the resection guide supported by the instrument support without inserting pins through the resection guide into the bone and without removing the resection guide from the support frame.

The surgeon can then perform bone resections using a cutting instrument such as a bone saw (not shown) for example. Other cutting instruments, such as a rotating burr could also be used. Once the resections of this first bone are complete, the surgeon can select another guide structure (such as a distal femoral resection guide) designed for resection of the other bone of the joint and mount this guide structure on the support frame. The surgeon may then release the actuators through operation of the switch 33 so that the arms 30, 32, 34 are again more flexible, and then position the support frame and second resection guide in the optimal position, alignment and orientation for the next bone resection. Setting of the position, alignment and orientation of the support frame with the second resection guide can be computer guided as well. Once the support frame and second resection guide are set in the optimal position, alignment and orientation for the next resection, the switch may again activated again to stiffen the arms 30, 32, 34. This process may be continued until all bone resections are complete. For a knee implant, the system may be used for all tibial, femoral and patellar resections. All of the steps involving the resection guides for the tibial, femoral and patellar resections can be performed without moving the moving the bases 22, 24.

If the leg stabilizing system of FIGS. 3 and 4 is used, the patient's leg can be fixed in flexion during part of the surgical procedure. When desired, the system can be released so that the surgeon can evaluate the patient with the leg in extension as well.

It should be appreciated that although the surgical technique described above relates particularly to knee arthroplasty, the same general steps can be followed for performing other resections at other joints. It will also be appreciated that instead of using computer navigation trackers, the surgical technique could employ standard mechanical alignment devices (such as alignment rods).

While only specific embodiments of the invention have been described and shown, it is apparent that various alternatives and modifications can be made thereto. Those skilled in the art will also recognize that certain additions can be made to the illustrative embodiment. It is, therefore, the intention in the appended claims to cover all such alternatives, modifications and additions as may fall within the true scope of the invention.

We claim:

1. A surgical instrument support system comprising:
   a support frame including a top plate having an inner edge and surfaces extending from the inner edge of the top plate to define an opening;
   a first arm and a first actuator, the first arm having first and second ends, the first end of the first arm being connected to the support frame and the second end of the first arm being connected to the first actuator, the first arm including a tension member a plurality of ball and socket members slidably strung along the tension member in series to form a plurality of articulatable linkages having a stiffness;
   a second arm and a second actuator, the second arm having first and second ends, the first end of the second arm being connected to the support frame and the second end of the first arm being connected to the second actuator, the second arm including a tension member and a plurality of ball and socket members slidably strung along the tension member in series to form a plurality of articulatable linkages having a stiffness;
   a third arm and a third actuator, the third arm having first and second ends, the first end of the third arm being connected to the support frame and the second end of the third arm being connected to the third actuator, the third arm including a tension member having a plurality of ball and socket members slidably strung along the tension member in series to form a plurality of articulatable linkages having a stiffness;
   a plurality of resection guides selectively mountable on the support frame, each resection guide including a top plate and a body, wherein the top plate and body of each resection guide are sized and shaped so that when the resection guide is mounted on the support frame the body fits within and is complementary with the opening of the support frame and the top plate of the resection guide contacts and is supported by the support frame, and wherein the top plate of at least one of the resection guides includes a pair of spaced parallel edges defining a through slot; and
   an inflatable cuff sized and shaped to be placed around a proximal portion of a patient's limb;
   wherein:
   activation of the first actuator changes the stiffness of the first arm;
   activation of the second actuator changes the stiffness of the second arm; and
   activation of the third actuator changes the stiffness of the third arm.

2. The surgical instrument support system of claim 1 further comprising a base and wherein at least one of the first, second and third actuators is connected to the base.

3. The surgical instrument support system of claim 2 wherein at least two of the first, second and third actuators is connected to the base.

4. A surgical instrument system for resecting a portion of a bone at a joint of a patient's limb, the system comprising:
   a proximal base sized and shaped to be mountable on the exterior of the patient's limb on the proximal side of the joint;
   a distal base sized and shaped to be mountable on the exterior of the patient's limb on the distal side of the joint;
   a support frame including a top plate having an inner edge and surfaces extending from the inner edge of the top plate to define an opening;
   a resection guide selectively mountable to the support frame, the resection guide including a top plate and a body sized and shaped so that when the resection guide is mounted on the support frame the body fits within and is complementary with the opening of the support frame and the top plate of the resection guide contacts and is supported by the support frame, the top plate of the resection guide including a pair of spaced parallel edges defining an elongate guide path;
   a first arm having first and second ends, the first end of the first arm being connected to the support frame and the second end of the first arm being connected to the proximal base, the first arm including a tension member having first and second ends and a plurality of ball and socket members slidably strung along the tension member to form a plurality of articulatable linkages;
   a second arm having first and second ends, the first end of the second arm being connected to the support frame and the second end of the first arm being connected to one of the bases, the second arm including a tension member having first and second ends and a plurality of ball and socket members slidably strung along the tension member to form a plurality of articulatable linkages;
   a third arm having first and second ends, the first end of the third arm being connected to the support frame and the second end of the third arm being connected to the distal base, the third arm including a tension member having first and second ends and a plurality of ball and socket members slidably strung along the tension member to form a plurality of articulatable linkages;
   a tensioning mechanism for increasing the tension in each tension member; and
   an inflatable cuff sized and shaped to be placed around a proximal portion of the patient's limb.

5. The system of claim 4 further comprising a second resection guide selectively mountable to the support frame, the second resection guide including a top plate and a body sized and shaped so that when the resection guide is mounted on the support frame the body fits within and is complementary with the opening of the support frame and the top plate of the resection guide contacts and is supported by the support frame, and wherein the top plate of the second resection guide includes a pair of spaced parallel edges defining an elongate guide path.

6. The system of claim 4 further comprising an actuator for simultaneously increasing the tension in the tension member of each arm.

7. The system of claim 4 wherein the support frame comprises spaced opposing portions and a connecting portion extending between the spaced opposing portions.

8. The system of claim 7 wherein the support frame comprises an annular member.

9. The system of claim 8 wherein the body of the resection guide is cylindrical in shape.

10. The system of claim 4 further comprising a cutting tool including a saw blade, wherein the elongate guide path comprises through slot sized and shaped to receive the saw blade.

11. The system of claim 4 further comprising a cutting instrument selected from the group consisting of a surgical burr and a milling device, wherein the elongate guide path further comprises a non-linear portion, the guide path defining the path of the cutting instrument.

12. The surgical instrument system of claim 4 wherein the resection guide comprises a tibial cutting block.

13. The system of claim 4 further comprising a plurality of computer navigation trackers.

14. The system of claim 13 further comprising a cutting tool including a saw blade, wherein the elongate guide path comprises a through slot sized and shaped to receive the saw blade and at least one of the computer navigation trackers includes a plate sized and shaped to be received in the through slot of the cutting guide.

15. The system of claim 14 wherein at least one of the computer navigation trackers comprises an electromagnetic sensor.

16. The system of claim 4 further comprising an inflatable cuff sized and shaped to be placed around a distal portion of the patient's limb.

17. The system of claim 4 wherein the proximal base comprises an elongate strap sized and shaped to be wrapped around a portion of the proximal portion of the patient's limb.

18. The system of claim 4 wherein the proximal base comprises an elongate strap sized and shaped to be wrapped around the inflatable cuff.

19. The system of claim 4 wherein the distal base comprises an elongate strap sized and shaped to be wrapped around a portion of the distal portion of the patient's limb.

20. The system of claim 16 wherein the distal base comprises an elongate strap sized and shaped to be wrapped around the inflatable cuff.

21. The surgical instrument support system of claim 1 wherein the top plates of the resection guides include through holes to receive pins to fix the resection guides to the bone.

22. The system of claim 4 wherein the top plate of the resection guide includes a plurality of through holes to receive pins to fix the resection guide to the bone.

* * * * *